US008796329B2

(12) United States Patent
Wallner et al.

(10) Patent No.: US 8,796,329 B2
(45) Date of Patent: Aug. 5, 2014

(54) METHOD FOR CONTROLLING ANGIOGENESIS IN ANIMALS

(75) Inventors: Barbara P. Wallner, Cohasset, MA (US); Philip B. Komarnitsky, Chestnut Hill, MA (US)

(73) Assignee: Ziopharm Oncology, Inc., Boston, MA (US)

( * ) Notice: Subject to any disclaimer, the term of this patent is extended or adjusted under 35 U.S.C. 154(b) by 0 days.

(21) Appl. No.: 11/906,137

(22) Filed: Sep. 28, 2007

(65) Prior Publication Data

US 2008/0139629 A1 Jun. 12, 2008

Related U.S. Application Data

(60) Provisional application No. 60/848,283, filed on Sep. 29, 2006, provisional application No. 60/860,147, filed on Nov. 20, 2006, provisional application No. 60/900,937, filed on Feb. 12, 2007.

(51) Int. Cl.
*C07F 9/00* (2006.01)
*A01N 55/02* (2006.01)
*A61K 31/285* (2006.01)

(52) U.S. Cl.
USPC .............................. 514/504; 556/71; 556/76

(58) Field of Classification Search
None
See application file for complete search history.

(56) References Cited

U.S. PATENT DOCUMENTS

| | | | |
|---|---|---|---|
| 2,349,729 A | 5/1944 | Hopkinson et al. | |
| 6,191,123 B1 | 2/2001 | Uckun et al. | |
| 6,482,815 B1 | 11/2002 | Uckun et al. | |
| 6,482,816 B1 | 11/2002 | Uckun et al. | |
| 6,911,471 B2 | 6/2005 | Zingaro et al. | |
| 6,995,188 B2 | 2/2006 | Zingaro et al. | |
| 7,405,314 B2 | 7/2008 | Zingaro et al. | |
| 7,619,000 B2 | 11/2009 | Zingaro et al. | |
| 2002/0013371 A1 | 1/2002 | Warrell et al. | |
| 2002/0183385 A1 | 12/2002 | Ellison et al. | |
| 2003/0176359 A1 | 9/2003 | Neuwelt et al. | |
| 2004/0028750 A1 | 2/2004 | Lu | |
| 2005/0131062 A1 | 6/2005 | Zingaro et al. | |
| 2006/0128682 A1* | 6/2006 | Zingaro et al. ................ | 514/184 |
| 2007/0183972 A1 | 8/2007 | Gutsch et al. | |

FOREIGN PATENT DOCUMENTS

| | | |
|---|---|---|
| EP | 1002537 | 10/1998 |
| SU | 188 971 A | 11/1966 |
| WO | WO-99/24029 | 5/1999 |
| WO | WO-01/21628 A1 | 3/2001 |
| WO | WO-03/003011 A1 | 1/2003 |
| WO | WO-03/057012 A2 | 7/2003 |
| WO | WO-2006/020048 A2 | 2/2006 |
| WO | WO-2007027344 A2 | 3/2007 |

OTHER PUBLICATIONS

Mandic et al. Tumor angiogenesis and endometrial cancer. Archieve of Oncology, 2002, 10(2): 79-81.*
Gupta (Postgrad. Med. J., 2005, 81: 236-242).*
Holland-Frei Cancer Medicine. 6th edition. Kufe DW, Pollock RE, Weichselbaum RR, et al., editors. Hamilton (ON): BC Decker; 2003. Electronic Resource. Retrieved on Apr. 25, 2010. [http://www.ncbi.nlm.nih.gov/books/NBK12544/].*
Nakamura et al. Dienogest, a synthetic steroid, suppresses both embryonic and tumor-cell induced angiogenesis. European Journal of Pharmacology, 386, 1999, 33-40.*
Don et al. A peptide trivalent arsenical inhibits tumor angiogeneis by perturbing mitochondrial function in angiogenic endothelial cells. Cancer Cell. May 2003, vol. 3.*
Constantinides et al. Vessel invasion by tumour cells. Virchows Archiv. A. Pathol. Anat. 1989, 415: 335-346.*
Passegue et al. Normal and leukemic hematopoiesis: are leukemias a stem cell disorder or a reacquisition of stem cell characteristics? Proceedings of the National Academy of Sciences of the United States of America. vol. 100, Arthur M. Sackler Colloquium on Regenerative Medicine. Sep. 30, 2003, pp. 11842-11849.*
International Search Report for PCT/US2007/021068 dated May 9, 2008.
American Conference of Governmental Industrial Hygienists, Inc. (ACGIH). Arsenic and soluble compounds, including arsine. Documentation of the Threshold Limit Values and Biological Exposure Indices, sixth edition, 1991.
Aslanidis, et al., "Methylarsino-substituted hydroxy carboxylate esters," Chemiker-Zeitung, 112(4):125-127 (1988).
Bachleitner-Hofmann et al., "Arsenic trioxide and ascorbic acid: synergy with potential implications for the treatment of acute myeloid leukaemia," Br. J. Haematol., 112(3):783-786 (2001).
Banks, et al., "Biomolecules Bearing the S- or SeAsMe2 Function: Amino Acid and Steroid Derivatives," Jr. of Medicinal Chemistry, American Chemical Society, 22(5):572-575 (1979).
Barber, Harry J., "Hydrolysis of arylthioarsinites Hydrolysis of arylthioarsinites," Jr. of the Chemical Society, Abstracts 1365-9 (1932).
Beckermann, "Determination of monovethylarsonic acid and dimethylarsinic acid by derivatization with thioglycolic acid methyl ester and gas-liquid chromatographic separation," Analytica Chimica Acta, 135(1):77-84 (1982).
Beliles, "The Metals," In *Patty's Industrial Hygiene and Toxicology, fourth edition* G.D. Clayton and F.E. Clayton, eds. John Wiley & Sons, Inc.: New York. pp. 1913-1925 (1994).
Caira, M.R., "Crystalline Polymorphism of Organic Compounds," Topics in Current Chemistry, 198:163-208 (1998).
Calleja and Warrell, "Differentiating agents in pediatric malignancies: all-trans-retinoic acid and arsenic in acute promyelocytic leukemia," Curr. Oncol. Rep., 2:519-523 (2000).
Chen, et al., "6-thio-and-seleno-alpha-D-glucose esters of dimethylarsinous acid," Carb. Res. 50:53-62 (1976).
Chen, et al., "Synthesis of 1- and 6-S and 1- and 6-Se-derivatives of 2-amino-2-deoxy-alpha/beta-D-glucopyrasone," J. Chemical Soc, Perkin Trans., 1:2287-2293 (1980).
Cullen, et al., "The metabolism of methylarsine oxide and sulfide," Applied Organometallic Chemistry, 3(1):71-78 (1989).

(Continued)

*Primary Examiner* — Anna Pagonakis
(74) *Attorney, Agent, or Firm* — Wilmer Cutler Pickering Hale and Dorr LLP

(57) ABSTRACT

Organic arsenical compounds are useful to inhibit angiogenesis in a variety of disease conditions.

20 Claims, 6 Drawing Sheets

(56) References Cited

OTHER PUBLICATIONS

Cullen, et al., "The reaction of methylarsenicals with thiols: some biological implications," Journal of Inorganic Biochemistry, 21(3):179-194 (1984).

Cuzick, et al., "Medicinal arsenic and internal malignancies," Br. J. Cancer, 45:904-911 (1982).

Daniel, et al., "Dimethylarsinous Acid Esters of 1-Thio- and -Selenogalactose, a New Class of Potential Carcinostatic Agents," Phosphorus and Sulfur, 4:179-185 (1978).

Emran, et al., "Synthesis and biodistribution of radioarsenic labeled dimethylarsinothiols: derivatives of pennicillamine and mercaptoethanol," International Journal of Nuclear Medicine and Biology, 11(3-4):259-261 (1984).

Fatouros, et al., "Preparation and properties of arsonolipid containing liposomes," Chemistry and Physics of Lipids, 109:75-89 (2001).

Forkner and McNair-Scott, "Arsenic as a therapeutic agent in chronic myeloid leukemia," JAMA, 97(1):3-6 (1931).

Geissler, et al., "In vivo effects of arsenic trioxide in refractory acute myeloid leukemia other than acute promyelocytic leukemia," Blood, 94:4230a (1999).

Goyer, "Toxic effects of metals" in *Casarett and Doull's Toxicology: The Basic Science of Poisons*, 5th edition. C.D. Klassen, ed. McGraw-Hill: New York, pp. 691-698 (1996).

Grignani, et al., "The acute promyelocytic leukemia-specific PML-RAR alpha fusion protein inhibits differentiation and promotes survival of myeloid precursor cells," Cell, 74:423-431 (1993).

Hosain, et al., "Synthesis of radioarsenic labeled dimethylchloroarsine for derivation of a new group of radiopharmceuticals," International Journal of Applied Radiation and Isotopes, 33(12):1477-1478 (1982).

Hughes and Kenyon, "Dose-dependent effects on the disposition of monomethylarsonic acid and dimethylarsinic acid in the mouse after intravenous administration," J. Toxicol. Environ. Health, 53(2):95-112 (1998).

IARC. Some metals and metallic compounds. IARC Monographs on the Evaluation of the Carcinogenic Risk of Chemicals to Man. vol. 23:39-141 (1980).

Ionov, et al., "Reaction of tertiary arsine sulfides with alkyl chlorocarbonates," Zhurnal Obshchei Khimii, 46(11):2555-2558 (1976).

Kala, et al., "The MRP2/cMOAT transporter and arsenic-glutathione complex formation are required for bilary excretion of arsenic," J. Biol. Chem., 275(43):33404-33408 (2000).

King and Ludford, "Relation between the constitution of arsenicals and their action on cell division," Journal of the Chemical Society Abstracts, 2086-2088 (1950).

Kitamura, et al., "New retinoids and arsenic compounds for the treatment of refractory acute promyelocytic leukemia: clinical and basic studies for the next generation," Cancer Chemother Pharmacol., 40 (Suppl):S36-S41 (1997).

Knock, et al., "The use of selected sulfhydryl inhibitors in a preferential drug attack on cancer," Surg. Gynecol. Obstet., 133:458-466 (1971).

Kober, et al., "Reaction of (dimethylamino)dimethylarsine with 1, 2-diols Reaction of (dimethylamino)dimethylarsine with 1, 2-diols," Zeitschrift Fuer Anorganische Und Allgemeine Chemie, 406(1):52-61 (1974).

Konig, A., et al., "Comparative activity of melarsoprol and arsenic trioxide in chronic B-cell leukemia lines," Blood 90:562-570 (1997).

Lallemand-Breitenbach, et al., "Retinoic acid and arsenic synergize to eradicate leukemic cells in a mouse model of acute promyelocytic leukemia," J. Exp. Med., 189:1043-1052 (1999).

Lam, et al., "Spectroscopic studies of arsenic (III) binding to *Escherichia coli* RI methyltransferase and to two mutants, C223S and W183F," Biochemistry, 31(43):10438-10442 (1992).

Lin, et al., "Methylarsenicals and arsinothiols are potent inhibitors of mouse liver thioredoxin reductase," Chemical Research in Toxicology, 12(10):924-930 (1999).

Mester, et al., "Speciation of dimethylarsinic acid and monomethylarsonic acid by gas chromatography-mass spectrometry," Jr. of Chromatography, 832(1+2):183-190 (1999).

Mountain, et al., "Chemotherapy studies in an animal tumor spectrum: II. Sensitivity of tumors to fourteen antitumor chemicals," Cancer Res., 26:181-206 (1966).

Rivi, et al., "Organic arsenical melarsoprol shows growth suppressive activity via programmed cell death on myeloid and lymphoid leukemia derived cell lines," Blood (Suppl), 88:68a (1996).

Rosenthal, et al., "The Synthesis and Characterization of Thio Sugar Esters of Diorganylarsinous Acids," Phosphorus and Sulfur, 9:107-116 (1980).

Rousselot, et al., "Use of arsenic trioxide (As2O3) in the treatment of chronic myelogenous leukemia: In vitro and in vivo studies," Blood, 94:4457a (1999).

Schoene, et al, "Speciation of arsenic-containing chemical warfare agents by gas chromatographic analysis after derivatization with thioglcolic acid methyl ester," Journal of Chromatography, 605(2):257-262 (1992).

Scott, et al., "Reactions of arsenic (III) and arsenic (V) species with glutathione," Chemical Research in Toxicology, 6(1):102-106 (1993).

Soignet, et al., "Clinical study of an organic arsenic melarsoprol, in patients with advanced leukemia," Cancer Chemother. Pharmacol. 44:417-421 (1999).

Soignet, et al., "Dose-ranging and clinical pharmacologic study of arsenic trioxide in patients with advanced hematologic cancers," Blood, 94:1247a (1999).

Styblo, et al., "Comparative inhibition of yeast glutathione reductase by arsenicals and arsenothiols," Chemical Research in Toxicology, 10(1):27-33 (1997).

Tallman, "Therapy of acute promyelocytic leukemia: all-tans retinoic acid and beyond," Leukemia, 12 (Suppl 1):S37-S40 (1998).

Tsalev, et al., "Flow-injection hydride generation atomic absorption spectrometric study of the automated on-line pre-reduction of arsenate, methylarsonate and dimethylarsinate and high-performance liquid chromatographic separation of their I-cysteine complexes," Talanta, 51(6):1059-1068 (2000).

Tsao, et al., "Optically Detected Magnetic Resonance Study of the Interaction of an Arsenic(III) Derivative of Cacodylic Acid with EcoRI Methyl Transferase," Biochemistry, 30(18):4565-72 (1991).

Vega, et al., "Differential effects of trivalent and pentavalent arsenicals on cell proliferation and cytokine secretion in normal human epiderman keratinocytes," Toxicology and Applied Pharmacology, 172(3):225-232 (2001).

Wiernik, et al., "Phase II trial of arsenic trioxide ($As_2O_3$) in patients with relapsed/refractory acute myeloid leukemia, blast crisis of CML or myelodysplasia," Blood, 94:2283a (1999).

Zhang, et al., "Arsenic trioxide treated 72 cases of acute promyelocytic leukemia," Chin. J. Hematol., 17:58-62 (1996).

International Search Report for PCT/US03/00281 dated May 21, 2004.

International Search Report for PCT/US2005/025192 dated Mar. 21, 2006.

International Search Report for PCT/US2006/029835 dated Oct. 25, 2007.

Supplementary European Search Report for EP 03 70 5662 dated Mar. 6, 2006.

Gillard, et al., "Amylo-1,6-glucosidase/4-α-glucanotransferase," The Journal of Biological Chemistry, 255(18): 8451-8457 (1980).

Zingaro et al., "Thio and Seleno Sugar Esters of Dialkylarsinous Acids," Carbohydrate Research, 29:147-152 (1973).

Zingaro, Ralph A., "Seleno and Thio Sugar Esters of Group VA Acids," Chemica Scripta, 8A: 51-57 (1975).

Hirano S. et al., "Cytotoxic effects of S-(dimethylarsino)-glutathione: a putative intermediate metabolite of inorganic arsenicals," Toxicology. Oct. 3, 2006 (Epub. Jul. 14, 2006), 227(1-2):45-52.

Sakurai T. et al., "Toxicity of a trivalent organic arsenic compound, dimethylarsinous glutathione in a rat liver cell line (TRL 1215)," Br J Pharmacol. Dec. 2006 (Epub. Oct. 16, 2006), 149(7):888-897.

(56) References Cited

OTHER PUBLICATIONS

Becker et al., "Angiogenesis and antiangiogenic therapy in endometriosis," Microvascular Research, vol. 74, pp. 121-130 (2007).

Ruhland et al., "Innovations in conservative endometriosis treatment: an updated review," Minerva Ginecol, vol. 63, pp. 247-259 (2011).

Becker et al., "Short synthetic endostatin peptides inhibit endothelial migration in vitro and endometriosis in a mouse model," Fertil Sterilm vol. 85, pp. 71-77 (2006).

Craig et al.: "Phase II trial of darinaparsin in leukemias and lymphomas," AACR Meeting Abstracts Online, Apr. 2008, XP000002657429, Retrieved from the Internet: URL:http://www.aacrmeetingabstracts.org/cgi/content/meeting_abstract/2008/1_Annual_Meeting/5527?maxtoshow=&hits=10&RESULTFORMAT=&author1=craig&andorexactfulltext=and&searchid=1&FIRSTINDEX=0&sortspec=relevance&resourcetype=HWCIT [retrieved on Aug. 22, 2011] (2 pages).

Adams, E. et al., "Chemistry of Organometalloid Complexes with Potential Antidotes: Structure of an Organoarsenic (III) Dithiolate Ring," Inorganic Chemistry, vol. 29(8) 5 pages. (1990).

Conklin, S.D. et al., "Investigation of pH effects on the formation of methylated thio-arsenicals, and the effects of pH and temperature on their stability," J. Analytical Atomic Spect., vol. 23: 711-716 (2008).

Foye's Principal Medicinal Chemistry, Seventh Ed., Ed. Lemke and Williams (4 pages) (2013).

Hanahan, D. and Weinberg, R. "Hallmarks of Cancer: The Next Generation," Cell, vol. 144: 30 pages (2011).

Lin, G-F et al., "Arsenic-related skin lesions and glutathione S-transferase P1 A1578G (Ile105Val) polymorphism in two ethnic clans exposed to indoor combustion of high arsenic coal in one village," Pharmaco. Genomics, vol. 16(12): 863-871 (2006).

Loring, R.H. et al., "Aromatic trivalent arsenicals: covalent yet reversible reagents for the agonist binding site of nicotinic receptors," Mol. Brain Res., vol. 15: 113-120: 1992.

McStay, G.P. et al., "Role of critical thiol groups on the matrix surface of the adenine nucleotide translocase in the mechanism of the mitochondrial permeability transition pore," Biochem., vol. 367: 541-548 (2002).

Meanwell, N.A. "Synopsis of Some Recent Tactical Application of Bioisoteres in Drug Design," J. Med. Chem., vol. 54: 2529-2591 (2011).

* cited by examiner

Figure 1: A Compound of Formula (II) Activity in Human Endothelia and Fibroblast with Cell Viability Assay Figure 3: A Compound of Formula (II) Inhibits Human Endothelial Tube Formation Figure 4: A Compound of Formula (II) Oral vs. IP in Mouse Leukemia Model

METHOD FOR CONTROLLING ANGIOGENESIS IN ANIMALS

CROSS-REFERENCE TO RELATED APPLICATIONS

This application claims the benefit of U.S. Provisional Application No. 60/848,283, filed Sep. 29, 2006, U.S. Provisional Application No. 60/860,147, filed Nov. 20, 2006 and U.S. Provisional Application No. 60/900,937, filed Feb. 12, 2007, the specifications of which are hereby incorporated herein by reference in their entirety.

BACKGROUND OF THE INVENTION

Medical science has recognized that angiogenesis is an important factor in the initiation and/or proliferation of a large number of diverse disease conditions. Under normal physiological conditions, humans and other animals only undergo angiogenesis in very specific, restricted situations. For example, angiogenesis is normally observed in wound healing, fetal and embryonic development, and in the formation of the corpus luteum, endometrium and placenta. The process of angiogenesis has been found to be altered in a number of disease states, and in many instances, the pathological damage associated with the disease is related to uncontrolled angiogenesis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating new blood vessels. Creation of the new microvascular system can initiate or exacerbate disease conditions.

Persistent, unregulated angiogenesis occurs in a multiplicity of disease states, including tumor metastasis and abnormal growth by endothelial cells, and supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

The art has made many attempts to develop materials and therapies which are capable of controlling angiogenesis. However, many materials which appear promising in vitro have proven to be relatively ineffective when applied in vivo. Furthermore, many such materials have been found to be unstable, toxic, or otherwise difficult to employ. Consequently, there is a need for additional methods and materials capable of controlling angiogenesis in a reliable manner.

SUMMARY OF THE INVENTION

There is disclosed herein a method for controlling angiogenesis in an organism comprising administering an organic arsenical compound. In certain embodiments, the organic arsenical has a structure of formula (I) or a pharmaceutically acceptable salt thereof

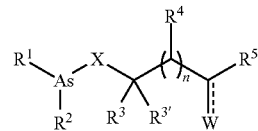

wherein
X is S or Se;
W is O, S, or (R)(R), where each occurrence of R is independently H or $C_{1-2}$alkyl;
n is 0 or 1;
$R^1$ and $R^2$ are each independently $C_{1-10}$alkyl;
$R^3$ is —H, $C_{1-10}$alkyl, or $C_{0-6}$alkyl-COOR$^6$;
$R^{3'}$ is H, amino, cyano, halogen, aryl, aralkyl, heteroaryl, heteroaralkyl, carboxyl, $C_{1-10}$alkyl, $C_{1-10}$alkenyl, or $C_{1-10}$alkynyl, preferably H;
$R^4$ is —OH, —H, —CH$_3$, amino, —OC(O)C$_{1-10}$aralkyl, —OC(O)C$_{1-10}$alkyl, or —OC(O)aryl;
$R^5$ is —OH, cyano, $C_{1-10}$alkoxy, amino, O-aralkyl, —OC(O)C$_{1-10}$aralkyl, —OC(O)C$_{1-10}$alkyl, —OC(O)aryl, or a glycine substituent; and
$R^6$ is H or $C_{1-10}$alkyl.

In certain embodiments, the organic arsenical has a structure of formula (II)

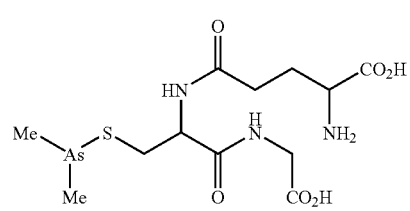

or a pharmaceutically acceptable salt thereof associated with pyridine hydrochloride, wherein the melting point of the compound in its crystalline form is greater than 125° C. In certain embodiments, the melting point of the compound in its crystalline form is greater than 160° C.

In certain embodiments, the organic arsenicals has a structure of formula (III)

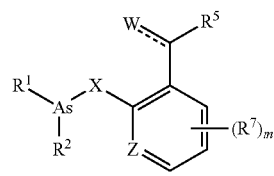

wherein
X is S or Se, preferably S;
W is O, S, or (R)(R), where each occurrence of R is independently H or a $C_{1-2}$alkyl, preferably O;
Z is CH or N, preferably N;
$R^1$ and $R^2$ are independently $C_{1-10}$alkyl, preferably $R^1$ and $R^2$ are independently selected from methyl, ethyl, propyl, and isopropyl; and
$R^5$ is —OH, cyano, $C_{1-10}$alkoxy, amino, O-aralkyl, O-aralkyl, —OC(O)C$_{1-10}$aralkyl, —OC(O)C$_{1-10}$alkyl, —OC(O)aryl, or a glycine substituent, preferably OH;

$R^6$ is H or $C_{1-10}$alkyl;
$R^7$ is selected from halogen, —OH, $C_{0-6}$alkyl-COOR$^6$, $C_{1-6}$alkyl, $C_{1-6}$alkoxy, amino, amido, cyano, and nitro;
m is an integer from 0 to 4, preferably 0.

In particular embodiments, the therapeutic treatment of the present invention is directed to diseases which are dependent upon neovascularization.

DETAILED DESCRIPTION OF THE INVENTION

Figure 1:
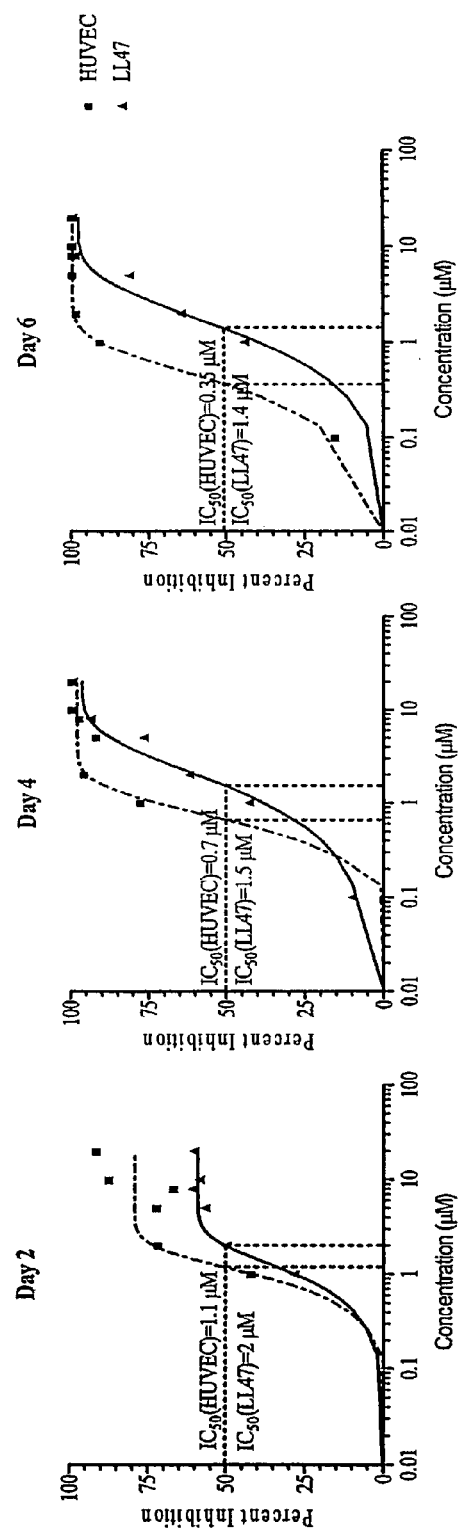
FIG. 1 shows the activity of a compound of formula (II) in human endothelia and fibroblast as measured with a cell viability assay.

The present invention provides methods for inhibiting angiogenesis comprising administering an organic arsenic compound. In certain embodiments, the organic arsenical has a structure of formula (I) or a pharmaceutically acceptable salt thereof

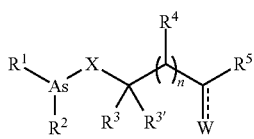

(I)

wherein
X is S or Se, preferably S;
W is O, S, or (R)(R), where each occurrence of R is independently H or a $C_{1-2}$alkyl, preferably O or (R)(R);
n is 0 or 1, preferably 1;
$R^1$ and $R^2$ are independently $C_{1-10}$alkyl, preferably $R^1$ and $R^2$ are independently selected from methyl, ethyl, propyl, and isopropyl;
$R^3$ is —H, $C_{1-10}$alkyl, or $C_{0-6}$alkyl-COOR$^6$;
$R^{3'}$ is H, amino, cyano, halogen, aryl, aralkyl, heteroaryl, heteroaralkyl, carboxyl, $C_{1-10}$alkyl, $C_{1-10}$alkenyl, or $C_{1-10}$alkynyl, preferably H;
$R^4$ is —OH, —H, —CH$_3$, amino, —OC(O)C$_{1-10}$aralkyl, —OC(O)C$_{1-10}$alkyl, or —OC(O)aryl;
$R^5$ is —OH, cyano, $C_{1-10}$alkoxy, amino, O-aralkyl, —OC(O)C$_{1-10}$aralkyl, —OC(O)C$_{1-10}$alkyl, —OC(O)aryl, or a glycine substituent; and
$R^6$ is H or $C_{1-10}$alkyl, preferably H.

In certain embodiments, W is (R)(R) and each occurrence of R is independently H or a $C_{1-2}$alkyl. In certain such embodiments, each occurrence of R is H.

In certain embodiments, $R^3$ is —H or $C_{0-6}$alkyl-COOR$^6$. In certain such embodiments, $R^3$ is selected from —COOR$^6$, —CH$_2$COOR$^6$, —CH$_2$CH$_2$COOR$^6$, —CH(CH$_3$)COOR$^6$, —CH(CH$_2$CH$_3$)COOR$^6$, or —CH$_2$CH$_2$CH$_2$COOR$^6$, wherein $R^6$ is $C_{1-10}$alkyl.

In certain embodiments, $R^3$ is $C_{1-10}$alkyl. In certain preferred such embodiments, $R^3$ is selected from methyl, ethyl, propyl, and isopropyl, preferably methyl.

In certain embodiments, $R^{3'}$ is selected from amino, cyano, halogen, aryl, aralkyl, heteroaryl, heteroaralkyl, carboxyl, $C_{1-10}$alkyl, $C_{1-10}$alkenyl, and $C_{1-10}$alkynyl. In preferred such embodiments, $R^{3'}$ is selected from aryl, aralkyl, heteroaryl, heteroaralkyl, carboxyl, $C_{1-10}$alkenyl, and $C_{1-10}$alkynyl In certain embodiments, $R^4$ is selected from —OH, —H, —CH$_3$, —OC(O)C$_{1-10}$aralkyl, —OC(O)C$_{1-10}$alkyl, and —OC(O)aryl. In certain such embodiments, $R^4$ is selected from —OC(O)C$_{1-10}$aralkyl, —OC(O)C$_{1-10}$alkyl, and —OC(O)aryl.

In certain embodiments, $R^4$ is amino. In certain such embodiments, $R^4$ is NH$_2$.

In certain embodiments, $R^5$ is selected from cyano, $C_{1-10}$alkoxy, amino, O-aralkyl, —OC(O)C$_{1-10}$aralkyl, —OC(O)C$_{1-10}$alkyl, and —OC(O)aryl.

In certain embodiments, X is S, W is (R)(R), wherein each occurrence of R is H, n is 1, $R^1$ and $R^2$ are independently selected from methyl, ethyl, propyl, and isopropyl, $R^3$ and $R^{3'}$ are H, $R^4$ is selected from OH, —OC(O)C$_{1-10}$aralkyl, —OC(O)C$_{1-10}$alkyl, and —OC(O)aryl and, and $R^5$ is selected from OH, —OC(O)C$_{1-10}$aralkyl, —OC(O)C$_{1-10}$alkyl, and —OC(O)aryl. In certain such embodiments, $R^1$ and $R^2$ are the same and are together selected from methyl, ethyl, propyl, and isopropyl.

In certain embodiments, X is S, W is O, n is 1, $R^1$ and $R^2$ are both methyl, $R^3$ is selected from H and COOR$^6$, $R^{3'}$ is H, and $R^4$ is selected from H and a glutamine substituent, and $R^5$ is selected from OH and a glycine substituent. In certain such embodiments, $R^3$ is COOR$^6$, $R^4$ is H, $R^5$ is OH, and $R^6$ is H.

In certain embodiments, the organic arsenical of formula (I) is selected from

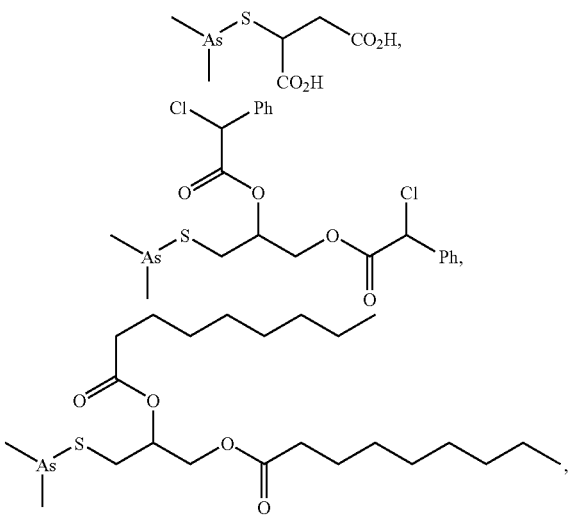

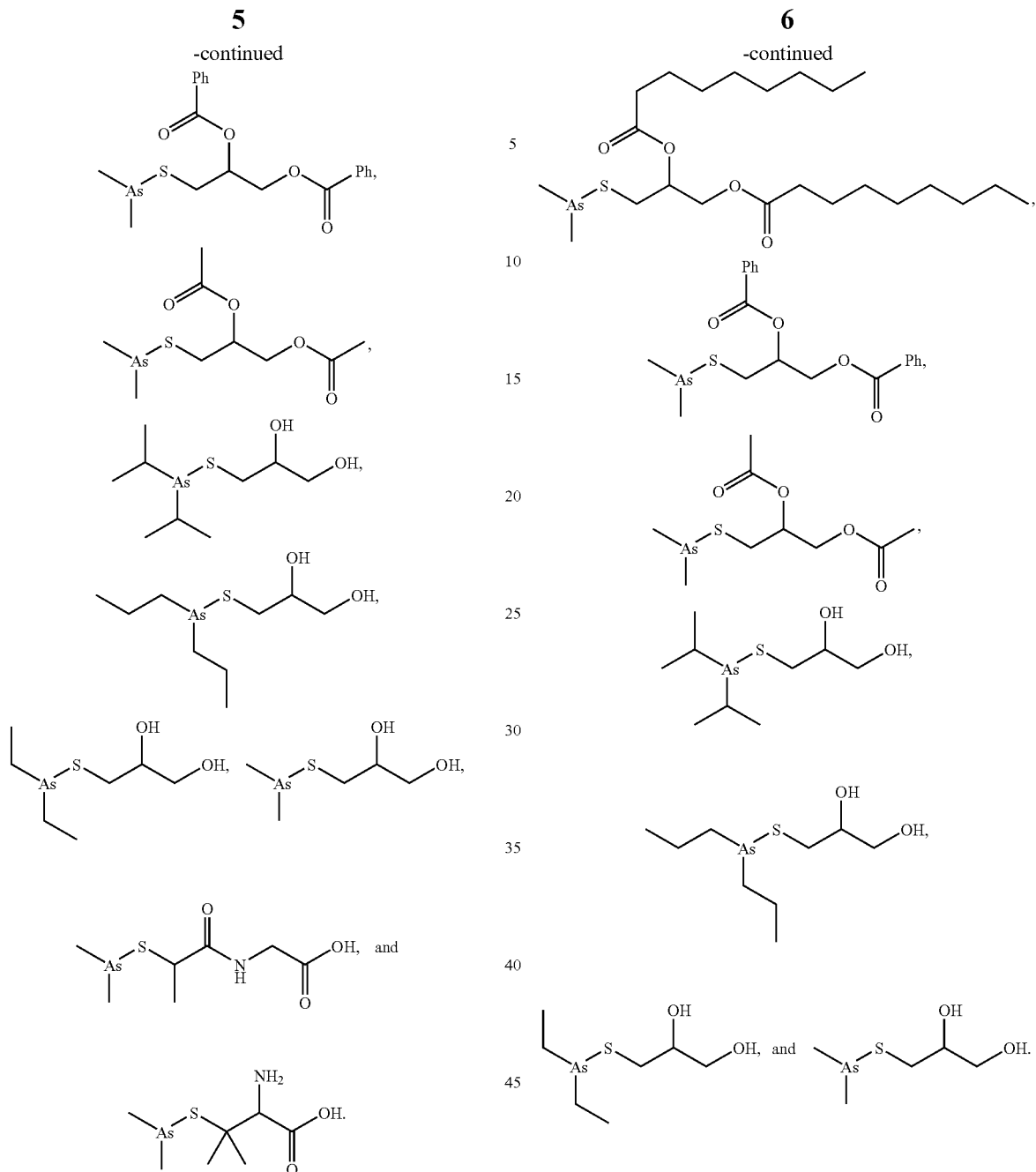
In certain embodiments, the organic arsenical of formula (I) is selected from
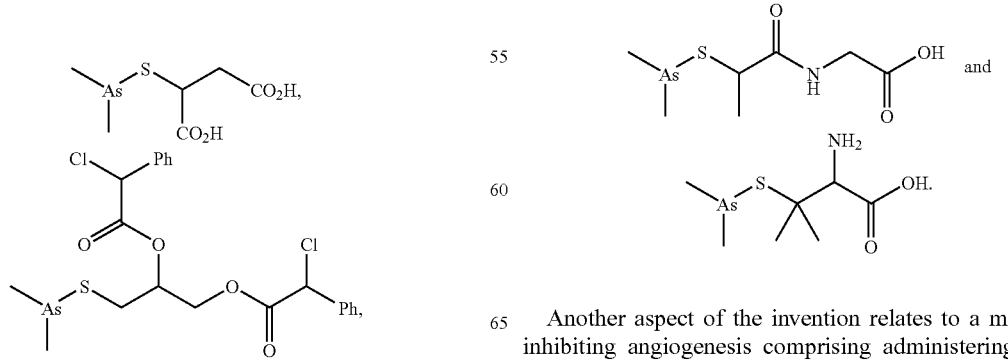
In certain embodiments, the organic arsenical of formula (I) is selected from
Another aspect of the invention relates to a method for inhibiting angiogenesis comprising administering a compound of formula (II)

(II)

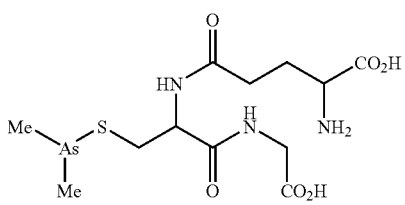

or a pharmaceutically acceptable salt thereof, wherein the melting point of the compound in its crystalline form is greater than 125° C., more preferably greater than 130° C., and most preferably greater than 135° C. In certain embodiments, the melting point of the compound in its crystalline form is in the range of about 125-150° C., preferably in the range of about 130-145° C., more preferably in the range of about 135-140° C. In certain embodiments, wherein a compound of formula (II) is associated with pyridine hydrochloride, the two compounds are present in a ratio of 1:0.9 to 1:1.1, preferably about 1:1. In certain such embodiments, the two compounds form a complex comprising one molecule of each compound.

In certain embodiments, the compound is a purified composition of formula (II) wherein the melting point of the compound in its crystalline form is greater than 160° C., preferably greater than 170° C., more preferably greater than 180° C. In certain embodiments, the melting point of the compound in its crystalline form is in the range of about 160-220° C., preferably in the range of about 180-220° C., more preferably in the range of about 185-195° C. In certain embodiments, a compound of formula (II) is substantially free of pyridine hydrochloride.

If a chiral center is present, all isomeric forms are within the scope of the invention. Regarding the stereochemistry, the Cahn-Ingold-Prelog rules for determining absolute stereochemistry are followed. These rules are described, for example, in *Organic Chemistry*, Fox and Whitesell; Jones and Bartlett Publishers, Boston, Mass. (1994); Section 5-6, pp 177-178, which section is hereby incorporated by reference.

In certain embodiments, the organic arsenicals are compounds having a structure of formula (III)

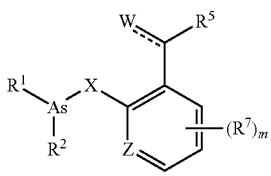

(III)

wherein
X is S or Se, preferably S;
W is O, S, or (R)(R), where each occurrence of R is independently H or a $C_{1-2}$alkyl, preferably O;
Z is CH or N;
$R^1$ and $R^2$ are independently $C_{1-10}$alkyl, preferably $R^1$ and $R^2$ are independently selected from methyl, ethyl, propyl, and isopropyl; and
$R^5$ is —OH, cyano, $C_{1-10}$alkoxy, amino, O-aralkyl, O-aralkyl, —OC(O)$C_{1-10}$aralkyl, —OC(O)$C_{1-10}$alkyl, —OC(O)aryl, or a glycine substituent, preferably OH;
$R^6$ is H or $C_{1-10}$alkyl;
$R^7$ is selected from halogen, —OH, $C_{0-6}$alkyl-COOR$^6$, $C_{1-6}$alkyl, $C_{1-6}$alkoxy, amino, amido, cyano, and nitro;
m is an integer from 0 to 4, preferably 0.

In certain embodiments, W is (R)(R) and each occurrence of R is independently H or a $C_{1-2}$alkyl. In certain such embodiments, each occurrence of R is H.

In certain embodiments, $R^5$ is selected from cyano, $C_{1-10}$alkoxy, amino, O-aralkyl, —OC(O)$C_{1-10}$aralkyl, —OC(O)$C_{1-10}$alkyl, and —OC(O)aryl.

In certain embodiments X is S, W is O, $R^1$ and $R^2$ are independently selected from methyl, ethyl, propyl, and isopropyl, and $R^5$ is OH. In certain such embodiments, $R^1$ and $R^2$ are the same and are together selected from methyl, ethyl, propyl, and isopropyl. In certain such embodiments, $R^1$ and $R^2$ are both methyl.

In certain embodiments, Z is N.
In certain embodiments, Z is CH.
In certain embodiments, the organic arsenical of formula (III) is selected from

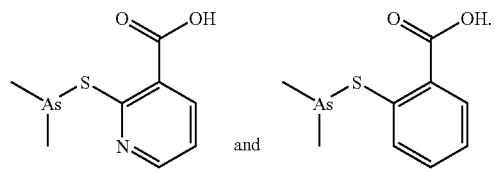

and

In certain embodiments, the organic arsenical of formula (III) is

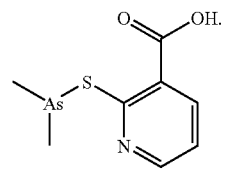

In other embodiments, the organic arsenicals are compounds having a structure of formula (IV)

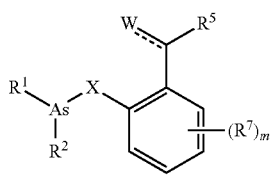

(IV)

wherein
X is S or Se, preferably S;
W is O, S, or (R)(R), where each occurrence of R is independently H or a $C_{1-2}$alkyl, preferably O;
$R^1$ and $R^2$ are independently $C_{1-10}$alkyl, preferably $R^1$ and $R^2$ are independently selected from methyl, ethyl, propyl, and isopropyl; and
$R^5$ is —OH, cyano, $C_{1-10}$alkoxy, amino, O-aralkyl, O-aralkyl, —OC(O)$C_{1-10}$aralkyl, —OC(O)$C_{1-10}$alkyl, —OC(O)aryl, or a glycine substituent, preferably OH;
$R^6$ is H or $C_{1-10}$alkyl;
$R^7$ is selected from halogen, —OH, $C_{0-6}$alkyl-COOR$^6$, $C_{1-6}$alkyl, $C_{1-6}$alkoxy, amino, amido, cyano, and nitro;
m is an integer from 0 to 4, preferably 0.

In certain embodiments, W is (R)(R) and each occurrence of R is independently H or a $C_{1-2}$alkyl. In certain such embodiments, each occurrence of R is H.

In certain embodiments, $R^5$ is selected from cyano, $C_{1-10}$alkoxy, amino, O-aralkyl, —OC(O)$C_{1-10}$aralkyl, —OC(O)$C_{1-10}$alkyl, and —OC(O)aryl.

In certain embodiments X is S, W is O, $R^1$ and $R^2$ are independently selected from methyl, ethyl, propyl, and isopropyl, and $R^5$ is OH. In certain such embodiments, $R^1$ and $R^2$ are the same and are together selected from methyl, ethyl, propyl, and isopropyl. In certain such embodiments, $R^1$ and $R^2$ are both methyl.

In certain preferred embodiments, the organic arsenical of formula (III) has the following structure

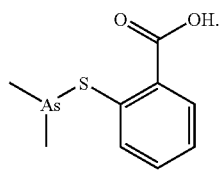

In certain embodiments, the organic arsenicals of the present invention have a structure of formula (V) or a pharmaceutically acceptable salt thereof

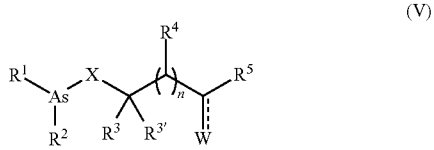

(V)

wherein

X is S or Se, preferably S;

W is O, S, or (R)(R), where each occurrence of R is independently H or a $C_{1-2}$alkyl, preferably O;

n is an integer from 2 to 20, preferably 9 to 14;

$R^1$ and $R^2$ are independently $C_{1-10}$alkyl, preferably $R^1$ and $R^2$ are independently selected from methyl, ethyl, propyl, and isopropyl;

$R^3$ is —H, $C_{1-10}$alkyl, or $C_{0-6}$alkyl-COOR$^6$, preferably H;

$R^{3'}$ is H, amino, cyano, halogen, aryl, aralkyl, heteroaryl, heteroaralkyl, carboxyl, $C_{1-10}$alkyl, $C_{1-10}$alkenyl, or $C_{1-10}$alkynyl, preferably H;

$R^4$ is —OH, —H, —CH$_3$, amino, —OC(O)$C_{1-10}$aralkyl, —OC(O)$C_{1-10}$alkyl, or —OC(O)aryl, preferably H;

$R^5$ is —OH, cyano, $C_{1-10}$alkoxy, amino, O-aralkyl, —OC(O)$C_{1-10}$aralkyl, —OC(O)$C_{1-10}$alkyl, or —OC(O)aryl, preferably OH or $C_{1-10}$alkoxy, more preferably OH; and $R^6$ is H or $C_{1-10}$alkyl, preferably H.

In certain embodiments, X is S, W is selected from 0 and (H)(H), preferably O, and n is an integer from 9 to 20. In certain such embodiments, n is an integer from 9 to 15.

In certain embodiments, $R^1$ and $R^2$ are independently selected from methyl, ethyl, propyl, and isopropyl. In certain embodiments, $R^1$ and $R^2$ are both methyl. In certain embodiments, $R^3$ and $R^{3'}$ are both H, $R^4$ is H, and $R^5$ is OH.

In certain embodiments, compounds of formula (V) are selected from

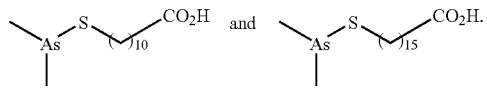

Compounds suitable for use in the subject compositions and methods of the present invention are disclosed in U.S. application Ser. Nos. 10/337,969, 11/252,966, 11/495,172, 60/759,218, and 60/763,008, all of which are incorporated by reference in their entirety.

DEFINITIONS

As used herein, the term "angiogenesis" means the generation and growth of new blood vessels into a tissue or organ.

The term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "$C_{1-6}$alkoxy" refers to an $C_{1-6}$alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "$C_{1-6}$aralkyl", as used herein, refers to a $C_{1-6}$alkyl group substituted with an aryl group.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

A "therapeutically effective amount" of a compound with respect to the subject method of treatment refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in manner to improve or stabilize a subject's condition.

Formulations

The compounds described above can be provided as pharmaceutically acceptable formulations using formulation methods known to those of ordinary skill in the art. These formulations can be administered by standard routes. In general, the combinations may be administered by the topical, transdermal, oral/nasal, rectal or parenteral (e.g., intravenous, subcutaneous or intramuscular) route. The combinations may be administered either by injection or by inhalation. In addition, the combinations may be incorporated into biodegradable polymers allowing for sustained release of the compound, the polymers being implanted in the vicinity of where drug delivery is desired, for example, at the site of a tumor. The biodegradable polymers and their use are described, for example, in detail in Brem et al., *J. Neurosurg.* 74:441-446 (1991).

The dosage of the compound will depend on the condition being treated, the particular compound, and other clinical factors such as weight and condition of the patient and the route of administration of the compound. It is to be understood that the present invention has application for both human and veterinary use.

For intravenous administration to humans, a dosage of between approximately 0.1-1000 mg/kg, preferably between approximately 1-500 mg/kg, and more preferably between approximately 1-100 mg/kg, is generally sufficient. In certain embodiments, an intravenous dosage of a subject compound is between 1 and 15 mg/kg, preferably between 5 and 12 mg/kg.

For oral administration to humans, a dosage of between approximately 1 to 4000 mg/kg, preferably between approximately 4 to 2000 mg/kg, and more preferably between approximately 4 to 400 mg/kg, is generally sufficient. In certain embodiments, an oral dosage of a subject compound is between 1 and 60 mg/kg, preferably between 5 and 45 mg/kg.

In particular embodiments, the method may comprise administering the composition one or more times daily. It is further contemplated that treatment methods may involve multiple administrations, e.g., at regular or irregular intervals. The method may comprise administering the compound daily such as by injection.

In certain embodiments, a compound of the invention may be administered at a cytotoxic dose, e.g., a dose sufficient to induce cell death in tumor cells.

In certain embodiments, a compound of the invention may be administered over an extended period of time, e.g., over one, two, three, or more months, or even over one, two, three, or more years at substantially regular intervals, e.g., with at least one administration every two weeks, such as daily, every other day, once a week, twice a week, etc. In certain embodiments, such extended treatments may comprise administering a compound of the invention at a dose lower than would be administered for acute uses, e.g., less than 50% of an acute dosage, such as a cytotoxic dosage. Such maintenance doses may be administered at substantially regular intervals, e.g., one or more times daily.

In certain embodiments, the subject invention comprises a regimen for treating a cancer, comprising administering a compound of the invention at cytotoxic doses for a first period of time, followed by administering a compound of the invention for a second period of time at a lower dosage, e.g., a dosage sufficient to inhibit angiogenesis, but insufficient to induce cell death in tumor cells. For example, a compound of the invention may be administered orally at a first dosage for the first period of time, and then orally at a second dosage that is less than half of the first dosage for the second period of time. In certain such embodiments, a compound of the invention is administered intravenously for the first period, and orally for the second period. In certain embodiments, a recovery period, in which a compound of the invention is not administered, occurs between the first period of time and the second period of time. Because less than 100% of a compound of the invention administered orally is absorbed by the human body, identical amounts of a compound of the invention administered intravenously and orally would result in a lower effective dose being administered in the oral dose.

The formulations include those suitable for oral, rectal, ophthalmic (including intravitreal or intracameral), nasal, topical (including buccal and sublingual), vaginal, intrathecal, parenteral (including subcutaneous, intramuscular, intravenous, intradermal, intratracheal, and epidural) or inhalation administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as hereinabove recited, or an appropriate fraction thereof, of the administered ingredient.

It should be understood that in addition to the ingredients particularly mentioned above, the formulations of the present invention may include other agents conventional in the art having regard to the type of formulation in question, for example, those suitable for oral administration may include flavoring agents.

Another aspect of the invention provides aerosol formulations suitable for inhalation delivery to the respiratory tract. The respiratory tract includes the upper airways, including the oropharynx and larynx, followed by the lower airways, which include the trachea followed by bifurcations into the bronchi and bronchioli. The upper and lower airways are called the conductive airways. The terminal bronchioli then divide into respiratory bronchioli which then lead to the ultimate respiratory zone, the alveoli, or deep lung. Herein, inhalation delivery may be oral and/or nasal. Examples of pharmaceutical devices for aerosol/inhalation delivery include metered dose inhalers (MDIs), dry powder inhalers (DPIs), and air-jet nebulizers. The human lungs can remove or rapidly degrade hydrolytically cleavable deposited aerosols over periods ranging from minutes to hours. In the upper airways, ciliated epithelia contribute to the "mucociliary excalator" by which particles are swept from the airways toward the mouth. See Pavia, D., "Lung Mucociliary Clearance," in *Aerosols and the Lung: Clinical and Experimental Aspects*, Clarke, S. W. and Pavia, D., Eds., Butterworths, London, 1984. In the deep lungs, alveolar macrophages are capable of phagocytosing particles soon after their deposition. See Warheit et al. *Microscopy Res. Tech.*, 26: 412-422 (1993); and Brain, J. D., "Physiology and Pathophysiology of Pulmonary Macrophages," in *The Reticuloendothelial System*, S. M. Reichard and J. Filkins, Eds., Plenum, New. York., pp. 315-327, 1985. The deep lung, or alveoli, are the primary target of inhaled therapeutic aerosols for systemic delivery.

Still another aspect of the invention relates to coated medical devices. For instance, in certain embodiments, the invention provides a medical device having a coating adhered to at least one surface, wherein the coating includes the subject compounds and preferably a polymer. Such coatings can be applied to surgical implements such as screws, plates, washers, sutures, prosthesis anchors, tacks, staples, electrical leads, valves, membranes. The devices include, but are not limited to, stents, catheters, implantable vascular access ports, blood storage bags, blood tubing, central venous catheters, arterial catheters, vascular grafts, intraaortic balloon pumps, heart valves, cardiovascular sutures, artificial hearts, a pacemaker, ventricular assist pumps, extracorporeal devices, blood filters, hemodialysis units, hemoperfusion units, plasmapheresis units, and filters adapted for deployment in a blood vessel. As discussed above, the coating according to the present invention comprises a polymer that is bioerodible or non-bioerodible. The choice of bioerodible versus non-bioerodible polymer is made based upon the intended end use of the system or device. In some embodiments, the polymer is advantageously bioerodible. For instance, where the system is a coating on a surgically implantable device, such as a screw, stent, pacemaker, etc., the polymer is advantageously bioerodible.

Although the invention contemplates using the subject compounds alone, or in combination with suitable excipients, dispersing agents, and the like, in some cases, one or more compounds of the present invention are combined with monomers for forming a polymer, and are mixed to make a homogeneous solution or a homogeneous dispersion in the monomer solution. The coating is then applied to a stent or other device according to a conventional coating process. In embodiments that employ polymerizable monomers, a crosslinking process may then be initiated by a conventional initiator, such as UV light. In other embodiments that utilize polymers in conjunction with a subject compound, one or more compounds of the present invention are combined with a polymer composition to form a solution or dispersion. The dispersion is then applied to a surface of a medical device and the polymer is cross-linked to form a solid coating. In other embodiments, one or more compounds of the present invention and a polymer are combined with a suitable solvent to form a solution or dispersion, which is then applied to a stent in a conventional fashion. The solvent is then removed by a conventional process, such as heat evaporation, with the result that the polymer and the subject compounds (together forming a sustained-release drug delivery system) remain on the stent or other device as a coating.

A stent is commonly used as a tubular structure left inside the lumen of a duct to relieve an obstruction. Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen. There are a multiplicity of different stents that may be utilized following coronary angioplasty. Although any number of stents may be utilized in accordance with the present invention, for simplicity, a limited number of stents will be described in exemplary embodiments. The skilled artisan will recognize that any number of stents may be utilized in connection with the present invention. In addition, as stated above, other medical devices may be utilized.

Stents may be fabricated utilizing any number of methods. For example, the stent may be fabricated from a hollow or formed stainless steel tube that may be machined using lasers, electric discharge milling, chemical etching or other means. The stent is inserted into the body and placed at the desired site in an unexpanded form. In one exemplary embodiment, expansion may be effected in a blood vessel by a balloon catheter, where the final diameter of the stent is a function of the diameter of the balloon catheter used.

It should be appreciated that a stent may be embodied in a shape-memory material, including, for example, an appropriate alloy of nickel and titanium or stainless steel. Structures formed from stainless steel may be made self-expanding by configuring the stainless steel in a predetermined manner, for example, by twisting it into a braided configuration. In this embodiment after the stent has been formed it may be compressed so as to occupy a space sufficiently small as to permit its insertion in a blood vessel or other tissue by insertion means, wherein the insertion means include a suitable catheter, or flexible rod.

On emerging from the catheter, the stent may be configured to expand into the desired configuration where the expansion is automatic or triggered by a change in pressure, temperature or electrical stimulation.

Uses

In certain embodiments, the compositions and methods of the present invention are useful for treating angiogenesis associated diseases and processes. Angiogenesis-associated diseases include, but are not limited to, angiogenesis-dependent cancer (e.g., cancers which require neovascularization to support tumor growth, e.g., renal, colon, or hepatic cancers), including, for example, solid tumors (e.g., renal cancer, pancreatic cancer, central nervous system cancer (spinal cord cancer), head and neck cancer, etc.), blood-borne tumors such as leukemias, and tumor metastases; benign tumors, for example hemangiomas, acoustic neuromas, neurofibromas, trachomas, and pyogenic granulomas; inflammatory disorders such as immune and non-immune inflammation; chronic articular rheumatism and psoriasis; ocular angiogenic diseases, for example, diabetic retinopathy, retinopathy of prematurity, macular degeneration, corneal graft rejection, neovascular glaucoma, retrolental fibroplasia, and rubeosis; Osler-Weber syndrome; myocardial angiogenesis; plaque neovascularization; telangiectasia; hemophiliac joints; angiofibroma; and wound granulation and wound healing; psoriasis, scleroderma; coronary collaterals; ischemic limb angiogenesis; corneal diseases; rubeosis; arthritis; diabetic neovascularization; fractures; vasculogenesis; hematopoiesis; and disorders associated with inappropriate or inopportune invasion of vessels such as restenosis, capillary proliferation in atherosclerotic plaques and osteoporosis.

One example of a disease associated with angiogenesis is ocular neovascular disease. This disease is characterized by invasion of new blood vessels into the structures of the eye such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Other diseases and conditions associated with corneal neovascularization include, but are not limited to, epidemic keratoconjunctivitis, vitamin A deficiency, contact lens overwear, atopic keratitis, superior limbic keratitis, pterygium keratitis sicca, Sjogren's, acne rosacea, phylectenulosis, syphilis, Mycobacteria infections, lipid degeneration, chemical burns, bacterial ulcers, fungal ulcers, herpes simplex infections, herpes zoster infections, protozoan infections, Kaposi's sarcoma, Mooren's ulcer, Terrien's marginal degeneration, marginal keratolysis, rheumatoid arthritis, systemic lupus, polyarteritis, trauma, Wegener's sarcoidosis, scleritis, Stevens-Johnson disease, pemphigoid, radial keratotomy, and corneal graft rejection.

Diseases associated with retinal/choroidal neovascularization include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme disease, systemic lupus erythematosus, retinopathy of prematurity, Eales disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other diseases include, but are not limited to, diseases associated with rubeosis (neovascularization of the ankle) and diseases caused by the abnormal proliferation of fibrovascular or fibrous tissue including all forms of proliferative vitreoretinopathy.

Another disease in which angiogenesis is believed to be involved is rheumatoid arthritis. The blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Factors associated with angiogenesis may also have a role in osteoarthritis. The activation of the chondrocytes by angiogenic-related factors contributes to the destruction of the joint. At a later stage, the angiogenic factors would promote new bone formation. Therapeutic intervention that prevents the bone destruction could halt the progress of the disease and provide relief for persons suffering with arthritis.

Chronic inflammation may also involve pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is prominent in solid tumor formation and metastasis. Angiogeneic factors have been found associated with several solid tumors such as rhabdomyosarcomas, retinoblastoma, Ewing sarcoma, neuroblastoma, and osteosarcoma. A tumor cannot expand without a blood supply to provide nutrients and remove cellular wastes. Tumors in which angiogenesis is important include solid tumors, and benign tumors such as acoustic neuroma, neurofibroma, trachoma and pyogenic granulomas. Prevention of angiogenesis could halt the growth of these tumors and the resultant damage to the animal due to the presence of the tumor.

It should be noted that angiogenesis has been associated with blood-borne tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

Angiogenesis is important in two stages of tumor metastasis. The first stage where angiogenesis stimulation is important is in the vascularization of the tumor, which allows tumor cells to enter the blood stream and to circulate throughout the body. After the tumor cells have left the primary site, and have settled into the secondary, metastasis site, angiogenesis must occur before the new tumor can grow and expand. Therefore, prevention or control of angiogenesis could lead to the prevention of metastasis of tumors and possibly contain the neoplastic growth at the primary site.

Knowledge of the role of angiogenesis in the maintenance and metastasis of tumors has led to a prognostic indicator for breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by therapeutic means can lead to cessation of the recurrence of the tumors.

Angiogenesis is also involved in normal physiological processes such as reproduction and wound healing. Angiogenesis is an important step in ovulation and also in implantation of the blastula after fertilization. Inhibition of angiogenesis could be used to treat or inhibit endometriosis, to induce amenorrhea, to block ovulation or to prevent implantation by the blastula, thereby preventing conception. In wound healing, excessive repair or fibroplasia can be a detrimental side effect of surgical procedures and may be caused or exacerbated by angiogenesis. Adhesions are a frequent complication of surgery and lead to problems such as small bowel obstruction.

Diseases associated with corneal neovascularization that can be treated according to the present invention include but are not limited to, diabetic retinopathy, retinopathy of prematurity, corneal graft rejection, neovascular glaucoma and retrolental fibroplasias, epidemic keratoconjunctivitis, vitamin A deficiency, contact lens overwear, atopic keratitis, superior limbic keratitis, pterygium keratitis sicca, Sjogren's, acne rosacea, phylectenulosis, syphilis, *Mycobacteria* infections, lipid degeneration, chemical burns, bacterial ulcers, fungal ulcers, herpes simplex infections, herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratotomy, and corneal graft rejection.

Diseases associated with retinal/choroidal neovascularization that can be treated according to the present invention include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme disease, systemic lupus erythematosus, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other diseases include, but are not limited to, diseases associated with rubeosis (neovascularization of the ankle) and diseases caused by the abnormal proliferation of fibrovascular or fibrous tissue including all forms of proliferative vitreoretinopathy, whether or not associated with diabetes.

Diseases associated with chronic inflammation can be treated by the compositions and methods of the present invention. Diseases with symptoms of chronic inflammation include inflammatory bowel diseases such as Crohn's disease and ulcerative colitis, psoriasis, sarcoidosis and rheumatoid arthritis. Angiogenesis is a key element that these chronic inflammatory diseases have in common. The chronic inflammation depends on continuous formation of capillary sprouts to maintain an influx of inflammatory cells. The influx and presence of the inflammatory cells produce granulomas and thus, maintain the chronic inflammatory state. Inhibition of angiogenesis by the compositions and methods of the present invention would prevent the formation of the granulomas and alleviate the disease.

The compositions and methods of the present invention can be used to treat patients with inflammatory bowel diseases such as Crohn's disease and ulcerative colitis. Both Crohn's disease and ulcerative colitis are characterized by chronic inflammation and angiogenesis at various sites in the gastrointestinal tract. Crohn's disease is characterized by chronic granulomatous inflammation throughout the gastrointestinal tract consisting of new capillary sprouts surrounded by a cylinder of inflammatory cells. Prevention of angiogenesis by the compositions and methods of the present invention inhibits the formation of the sprouts and prevents the formation of granulomas.

Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, non-specific, inflammatory and ulcerative disease arising in the colonic mucosa and is characterized by the presence of bloody diarrhea.

The inflammatory bowel diseases also show extraintestinal manifestations such as skin lesions. Such lesions are characterized by inflammation and angiogenesis and can occur at many sites other than the gastrointestinal tract. The compositions and methods of the present invention are also capable of treating these lesions by preventing the angiogenesis, thus reducing the influx of inflammatory cells and the lesion formation.

Sarcoidosis is another chronic inflammatory disease that is characterized as a multisystem granulomatous disorder. The granulomas of this disease may form anywhere in the body and thus the symptoms depend on the site of the granulomas and whether the disease is active. The granulomas are created by the angiogenic capillary sprouts providing a constant supply of inflammatory cells.

The compositions and methods of the present invention can also treat the chronic inflammatory conditions associated with psoriasis. Psoriasis, a skin disease, is another chronic and recurrent disease that is characterized by papules and plaques of various sizes. Prevention of the formation of the new blood vessels necessary to maintain the characteristic lesions leads to relief from the symptoms.

Another disease which can be treated according to the present invention is rheumatoid arthritis. Rheumatoid arthritis is a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Other diseases that can be treated according to the present invention are hemangiomas, Osler-Weber disease, or hereditary hemorrhagic telangiectasia, solid or blood-borne tumors and acquired immune deficiency syndrome.

Restenosis is another disease that can be inhibited or treated by the compositions and methods of the present invention. Restenosis is a process of smooth muscle cell (SMC) migration and proliferation at the site of percutaneous transluminal coronary angioplasty which hampers the success of angioplasty. The migration and proliferation of SMCs during restenosis can be considered a process of angiogenesis which may be controlled by the present methods. Therefore, the invention contemplates inhibition of restenosis by inhibiting angiogenesis according to the present methods in a patient following angioplasty procedures.

Similar to restenosis, atherosclerosis is a disease that is associated with inappropriate or inopportune invasion of vessels. For example, in atherosclerotic plaques, proliferation of capillaries is common and is considered a process of angiogenesis. Therefore, the compositions and methods of the present invention can be used to inhibit growth of atherosclerotic plaques.

Combination Therapy

It is an aspect of this invention that the organic arsenical can be used in combination with another agent or therapy method, preferably another cancer treatment. The organic arsenical may precede or follow the other agent treatment by intervals ranging from minutes to weeks. In embodiments where the other agent and expression construct are applied separately to the cell, one would generally ensure that a significant period of time did not elapse between the time of each delivery, such that the agent and expression construct would still be able to exert an advantageously combined effect on the cell. For example, in such instances, it is contemplated that one may contact the cell, tissue or organism with two, three, four or more modalities substantially simultaneously (i.e., within less than about a minute) with the organic arsenical. In other aspects, one or more agents may be administered within about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, to about 48 hours or more prior to and/or after administering the organic arsenical. In certain other embodiments, an agent may be administered within of from about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20, to about 21 days prior to and/or after administering the organic arsenical. In some situations, it may be desirable to extend the time period for treatment significantly, however, where several weeks (e.g., about 1, about 2, about 3, about 4, about 5, about 6, about 7 or about 8 weeks or more) lapse between the respective administrations.

Various combinations may be employed, the organic arsenical is "A" and the secondary agent, which can be any other therapeutic agent, is "B":

A/B/A  B/A/B  B/B/A  A/A/B  A/B/B  B/A/A  A/B/B/B

B/A/B/B  B/B/B/A  B/B/A/B  A/A/B/B  A/B/A/B  A/B/B/A

B/B/A/A  A/B/A/A  B/A/A/B  A/A/A/B  B/A/A/A  A/B/A/A

A/A/B/A

As used herein, the phrase "conjoint administration" refers to any form of administration in combination of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in separate formulations, either concomitantly or sequentially. Thus, an individual who receives such treatment can have a combined (conjoint) effect of different therapeutic compounds. Known therapeutics for treating an inflammatory disease or condition are described in medical textbooks such as Harrisons, Principles of Internal Medicine (McGraw Hill, Inc., New York). The particular therapeutic used depends on the nature of the disease or condition being treated.

Inhibition of tumor tissue angiogenesis is a particular embodiment of the present invention because of the important role neovascularization plays in tumor growth. In the absence of neovascularization of tumor tissue, the tumor tissue does not obtain the required nutrients, slows in growth, ceases additional growth, regresses and ultimately becomes necrotic resulting in killing of the tumor. Therefore, the present invention provides compositions and method for inhibiting tumor neovascularization by inhibiting tumor angiogenesis. The present invention can also particularly effective against the formation of metastases because: (1) their formation requires vascularization of a primary tumor so that the metastatic cancer cells can exit the primary tumor; and (2) their establishment in a secondary site requires neovascularization to support growth of the metastases.

In a related embodiment, the invention contemplates the practice of the method in conjunction with other therapies such as conventional chemotherapy directed against solid tumors and for control of establishment of metastases. The administration of the subject angiogenesis inhibitor is typically conducted during or after chemotherapy, although it is preferably to inhibit angiogenesis after a regimen of chemotherapy at times where the tumor tissue will be responding to the toxic assault by inducing angiogenesis to recover by the provision of a blood supply and nutrients to the tumor tissue. In addition, it is preferred to administer the angiogenesis inhibitors after surgery, e.g. where a solid tumor has been removed, as a prophylaxis against metastases.

A wide array of conventional compounds have been shown to have anti-tumor activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-tumor compounds induce undesirable side effects. In many cases, when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

Therefore, organic arsenicals as disclosed herein may be conjointly administered with a conventional anti-tumor compound. Conventional anti-tumor compounds include, merely to illustrate: aminoglutethimide, amsacrine, anastrozole, asparaginase, bcg, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

The conventional anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxanes (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, mechlorethamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (such as TNP-470, genistein, angiostatin, squalamine, captopril, combrestatin-A4, vitaxin, marimastat, neovastat, arresten, canstatin, tumstatin, thrombospondin 1, and endostatin) and growth factor inhibitors (vascular endothelial growth factor (VEGF) inhibitors such as bevacizumab (Avastin), SU11248, PTK787, and BAY 43-9006, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylprednisolone, prednisone, and prednisolone); growth factor signal transduction kinase inhibitors; mitochondrial dysfunction inducers and caspase activators; and chromatin disruptors. In certain preferred embodiments, a compound of the invention is administered conjointly (e.g., simultaneously or at different times) with an anti-angiogenic compound that works via a different biological pathway, such as VEGF inhibition or kinase inhibition. While not wishing to be limited to any particular mechanism, it is believed that the compounds of the invention act by disrupting mitochondrial function and inducing apoptosis.

In certain aspects, the methods and compositions of the present invention are also useful for modulating physiological processes associated with angiogenesis, for example, ovulation, menstruation, and placentation, or to treat or prevent endometriosis. The angiogenesis inhibiting proteins of the present invention are useful in the treatment of disease of excessive or abnormal stimulation of endothelial cells. These diseases include, but are not limited to, intestinal adhesions, atherosclerosis, scleroderma, and hypertrophic scars, i.e., keloids. They are also useful in the treatment of diseases that have angiogenesis as a pathologic consequence such as cat scratch disease (*Rochele minalia quintosa*) and ulcers (*Helicobacter pylori*).

As described herein, any of a variety of tissues, or organs comprised of organized tissues, can support angiogenesis in disease conditions including skin, muscle, gut, connective tissue, joints, bones and the like tissue in which blood vessels can invade upon angiogenic stimuli.

Thus, in one related embodiment, a tissue to be treated is an inflamed tissue and the angiogenesis to be inhibited is inflamed tissue angiogenesis where there is neovascularization of inflamed tissue. In this class, the method contemplates inhibition of angiogenesis in arthritic tissues, such as in a patient with chronic articular rheumatism, in immune or non-immune inflamed tissues, in psoriatic tissue and the like.

In another related embodiment, a tissue to be treated is a retinal tissue of a patient with a retinal disease such as diabetic retinopathy, macular degeneration or neovascular glaucoma and the angiogenesis to be inhibited is retinal tissue angiogenesis where there is neovascularization of retinal tissue.

In an additional related embodiment, a tissue to be treated is a tumor tissue of a patient with a solid tumor, a metastasis, a skin cancer, a breast cancer, a hemangioma or angiofibroma and the like cancer, and the angiogenesis to be inhibited is tumor tissue angiogenesis where there is neovascularization of a tumor tissue. Typical solid tumor tissues treatable by the present methods include lung, pancreas, breast, colon, laryngeal, ovarian, and the like tissues.

EXAMPLES

1) CellTiter-Glo Viability Assays for Both HUVEC and LL47

CellTiter-Glo Luminescent Cell Viability Assay (Promega Corporation) is based on quantification of ATP levels in cell cultures. The amount of ATP produced in cell culture reflects the number of viable cells. Hence, this assay is often used to estimate cell proliferation and cytotoxic effects of test compounds. HUVECs and LL47 cells were seeded in 96-well plates in their growth medium. After 24 hours, various doses of the compound of formula (II) were added to both cultures side by side, having six replicates for each dose. At different treatment time points, CellTiter-Glo reagent were added to the cultures following the manufacturer's instructions; luminescence signals were measured with an EnVision™ Multi-label Reader (Perkin Elmer, Wellesley, Mass.) The blank control groups were given saline vehicle only, and positive control groups were given 10 µM T-araC (provided by Southern). Data was analyzed for the mean and standard deviation for each treatment condition. $IC_{50}$ values of the compound of formula (II) against HUVEC and LL47 cell cultures were determined based on the dose response curves as shown in FIG. 1. There were several test drug concentrations with three treatment time points (2, 4, and 6 days). For the 6-day assay experiment, the culture media with different test concentration treatments was exchanged at Day 4.

| Compound of Formula (II) | Day 2 | Day 4 | Day 6 |
|---|---|---|---|
| $IC_{50}$ in HUVEC (Endothelia) | <1.5 mM | <1 mM | <0.5 mM |
| $IC_{50}$ in LL47 (Fibroblast) | <5 mM | <2 mM | <1.5 mM |

2) 3H-thymidine—Thy Incorporation Assay for HUVEC

Figure 2:
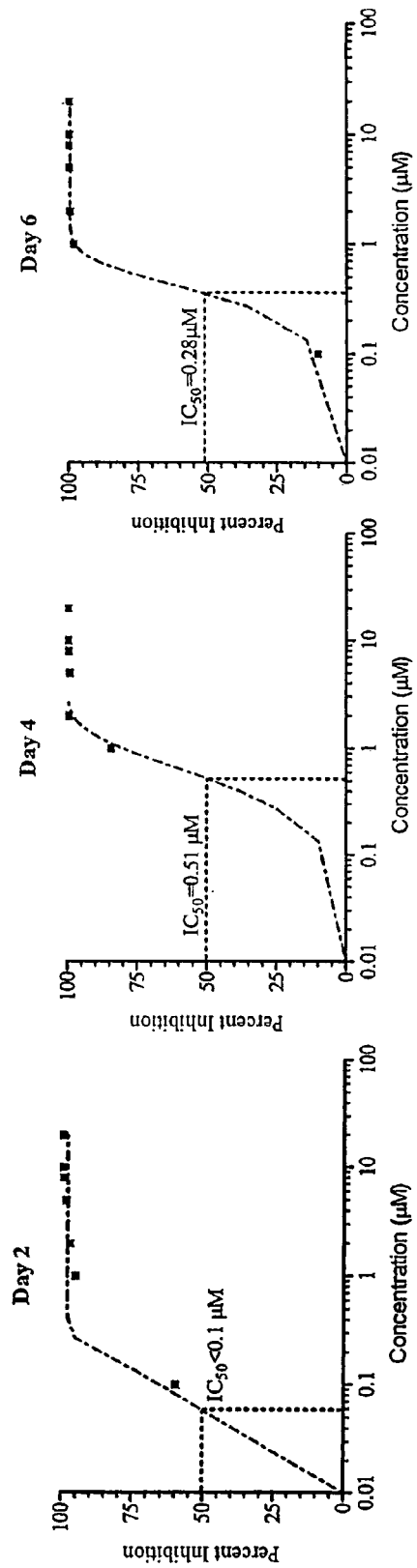
FIG. 2 shows the activity of a compound of formula (II) in human endothelia as measured with a $^3$H-thymidine incorporation assay.

HUVEC cultures were seeded and treated in 96-well plates, as described above for the CellTiter-Glo viability assay. After treatment of HUVEC cultures with the compound of formula (II), 96-well plates were pulsed with 1 µCi of $^3$H-thymidine for the final 6-18 hours of culture and then harvested with a semiautomatic cell harvester onto filters that bind the DNA. Samples were counted in a PerkinElmer Microbeta scintillation and luminescence counter (Trilux) to determine the amount of 3H-TdR uptake. The data was then transferred and processed using an Excel spreadsheet program to provide for the mean and standard deviation for % of control values. The results were analyzed by calculating $IC_{50}$ values and including a table showing % of control values for each compound tested. There were several test drug concentrations with three treatment time points (2, 4, and 6 days) and 6 replicates for each test concentration as shown in FIG. 2. For the 6-day assay experiment, the culture media with different test concentration treatments was exchanged at Day 4.

| Compound of Formula (II) | Day 2 | Day 4 | Day 6 |
|---|---|---|---|
| $IC_{50}$ in HUVEC (Endothelia) | <0.1 mM | <1 mM | <0.5 mM |

3) Endothelial Tube-Formation Assay

Figure 3:
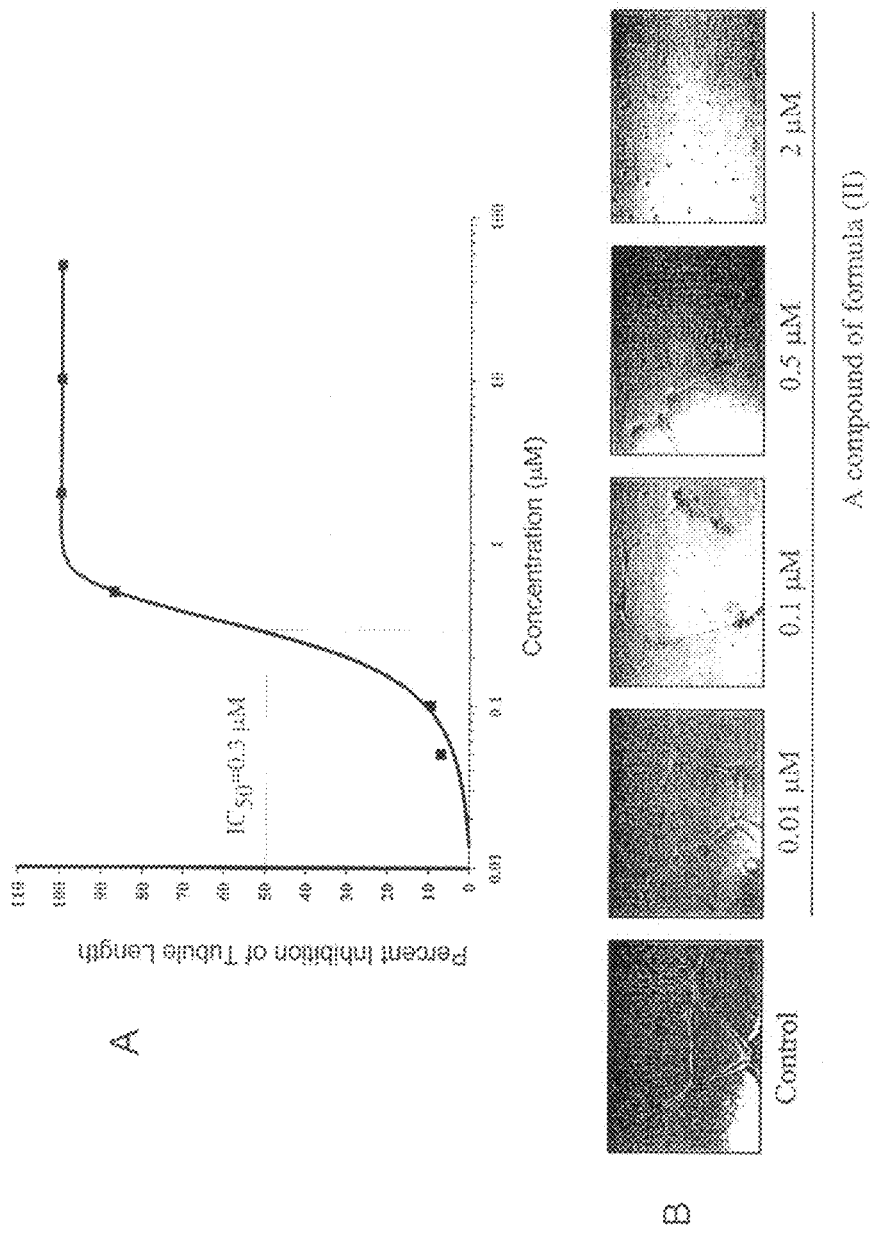
FIG. 3A shows the activity of a compound of formula (II) as measured with a human endothelial tube formation assay.
FIG. 3B shows endothelial tubes examined under an inverted light microscope.

Human endothelial cells were cultured in vitro on Extracellular Matrix, which stimulates the attachment and differentiation of endothelial cells into tubules. The endothelial cell tube formation assay is based on this phenomenon. HUVECs were seeded in a 96-well culture plate coated with Extracellular Matrix and then treated with test compound in the full growth medium. The same concentrations of the compound of formula (II) were tested together with negative and positive controls. The cells were allowed to form endothelial tubes for about 18 hours and then were examined under an inverted light microscope as shown in FIG. 3B. Two microscopic view fields per culture were photographed and quantitatively analyzed for an average tubule length using image analysis software (Image Pro Plus). Triplicate cell cultures were carried out for each test concentration and the controls. $IC_{50}$ values were calculated based on the dose curve as shown in FIG. 3A.

4) Matrigel Plug In Vivo Assay

Female C57BL/6 mice around 10-weeks old and Matrigel Matrix High Concentration (from Becton Dickinson) mixed with 50 ng/mL VEGF, 50 ng/mL FGFb, and heparin 3 ng/mL as angiogenic stimuli were used for the Matrigel Plug experiments. There were two groups of mice, five mice in each group, with one group serving as a control and the second group expected to be treated once daily for 9 days with a compound of formula II at 100 mg/kg/dose (0.2 mL/10 g of body weight) by intravenous (i.v.) injection. The control group received oral saline as a vehicle. Each mouse received two Matrigel plugs. On Day 0, 500 µL Matrigel at 4° C. was subcutaneously injected to each side of the mouse, wherein the injection area was shaved. To increase the contact area of injected Matrigel into subcutaneous tissues and form a round shape plug, a wide subcutaneous pocket was formed by swaying the needle point right and left after a routine subcutaneous insertion. The injection was done rapidly with an appropriate size needle (21 G-25 G) to ensure the entire contents of the syringe were delivered in one plug. The injected Matrigel rapidly formed a single solid gel plug. Mice from the i.v. dosing group received a total of 7 doses of a compound of formula (II) instead of the originally planned 9 doses (doses 6 and 8 were skipped because of higher than expected toxicity of a compound of formula II to C57BL/6 mice). Plugs from each group were collected at Day 12. The mice were euthanized and the mouse skin was pulled back to expose the plug. The plugs were dissected out and fixed in 10% formalin for histological analysis. Sections of 5 µm from paraffin-embedded plugs were stained with H&E. Blood vessel density in a cross sectional area of each Matrigel plug was analyzed using Image Pro-Plus software. For each group of mice, at least six Matrigel plugs were quantitatively analyzed to assess any statistical significant difference of microvessel density between groups. The quantitation of microblood vessel density using a compound of formula (II) is shown below.

| Animal | Control | Compound of Formula (II) Intravenous Injection |
|---|---|---|
| #1 | 28 | 3 |
| #2 | 24 | 2 |
| #3 | 128 | 2 |
| #4 | 21 | 0 |
| #5 | 43 | |
| Average | 48.8 | 1.75 |
| SD | 45.07 | 1.26 |
| SE | 20.16 | 0.63 |
| p value | 0.04 | |

5) Response of IP Implanted P388 Murine Leukemia to IP and PO Administration of the Compound of Formula (II)

Mice were implanted ip with one million cells of P388 murine leukemia using a 23-gauge needle. The P388 tumor line was maintained as an in vivo passage. The day of tumor implantation was designated as day 0, with treatment beginning on day 1 following tumor implantation. A sufficient number of mice were implanted so that animals with body weights in a range as narrow as possible were selected for the trial.

The compound of formula (II) was formulated in saline on the first day of treatment (day 1) at a concentration of 40 mg/mL. This solution was then diluted to the lower dosing concentrations of 30, 20, and 5 mg/mL. Enough of the compound of formula (II) was prepared on day 1 for the entire dosing period. Each dosing solution was then aliquoted for daily treatments, frozen at −20° C., and thawed on each day of injection. All injections were administered on the basis of exact body weight with the injection volume being 0.2 mL/10 g body weight.

The study consisted of four treatment groups of eight mice per group and one vehicle-treated control group with ten mice, for a total of 42 mice on the first day of treatment. The study design called for the compound of formula (II) to be administered once a day for nine consecutive days (qld×9) by oral gavage at dosages of 800, 600, and 400 mg/kg/dose and by ip injection at a dosage of 100 mg/kg/dose. The control group (group 1) was treated with the vehicle (saline), which was administered po on a qld×9 injection schedule.

The study was terminated 17 days after tumor implantation. Any animal that became moribund was euthanized prior to study termination.

Number of nonspecific deaths, median days of death, and the increase in lifespan based on the median day of death and expressed as a percentage (% ILS).

The individual animals' survival time was used as the endpoint in a life tables analysis (stratified Kaplan-Meier estimation followed by the Mantel-Haenszel log-rank test) in order to statistically compare the survival data between groups. A life tables analysis allows one to compare the survival data between the groups using the animals that did not reach the endpoint by censoring them.

The median day of death in the vehicle-treated control group was 11.5, with all deaths occurring between days 9 and 12. Ascites was present in all animals. No treatment-related deaths were observed in the group receiving treatment with the lowest dosage tested by po administration, 400 mg/kg/dose. All animals in the group completed the treatment regimen, but died between days 13 and 17 with ascites present. The median day of death for the group was 15.0 with an ILS of 30%, which was statistically different from the vehicle-treated control group (p=0.000).

Treatment with the compound of formula (II), given by ip injection at a dosage of 100 mg/kg/dose administered qld×9, was tolerated without treatment-related deaths. There was an 8% (2 g) loss in mean body weight. The median day of death was 14.5 with all deaths in the group occurring between days 13 and 16 with ascites present in all animals. The ILS value for the group was 26%, which was statistically different from the vehicle-treated control group (p=0.000) but not different from the po dosage of 100 mg/kg/dose (p=0.231).

| Summary of Statistical Analysis | |
| --- | --- |
| Group Pairs | p Value |
| 1 vs. 4 | 0.000 |
| 1 vs. 5 | 0.000 |
| 4 vs. 5 | 0.231 |

Figure 4:
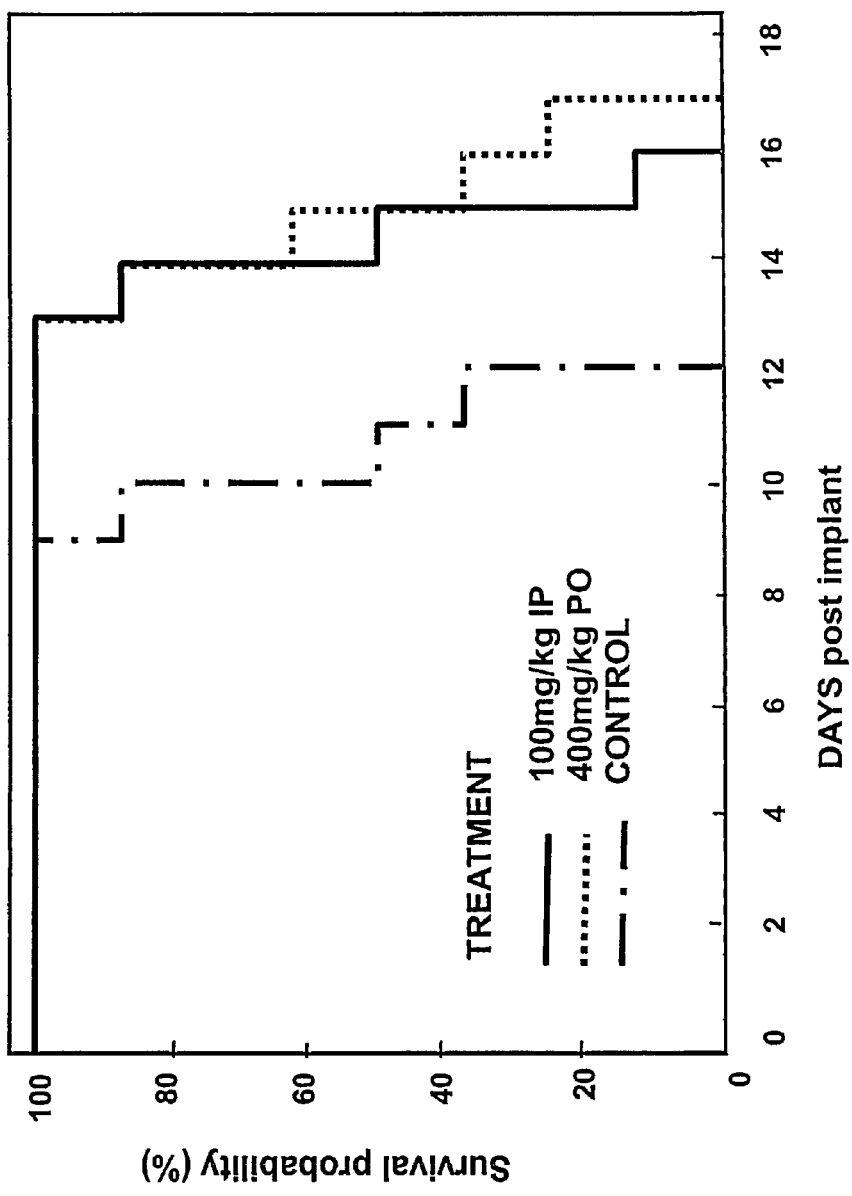
FIG. 4 shows results of treatment with the compound of formula (II) at dosages of 400 mg/kg/dose, po, and 100 mg/kg/dose, ip, versus vehicle in the ip implanted p388 murine leukemia model.

The results of treatment with the compound of formula (II) at dosages of 400 mg/kg/dose, po, and 100 mg/kg/dose, ip, versus vehicle are shown in FIG. 4. Treatment with the dosage of 400 mg/kg/dose administered po was tolerated and elicited a minimal increase in lifespan. Treatment with the compound of formula (II), administered ip at a dosage of 100 mg/kg/dose, was tolerated and resulted in a minimal increase in lifespan.

6) Matrigel Plug In Vivo Assay

Figure 5:
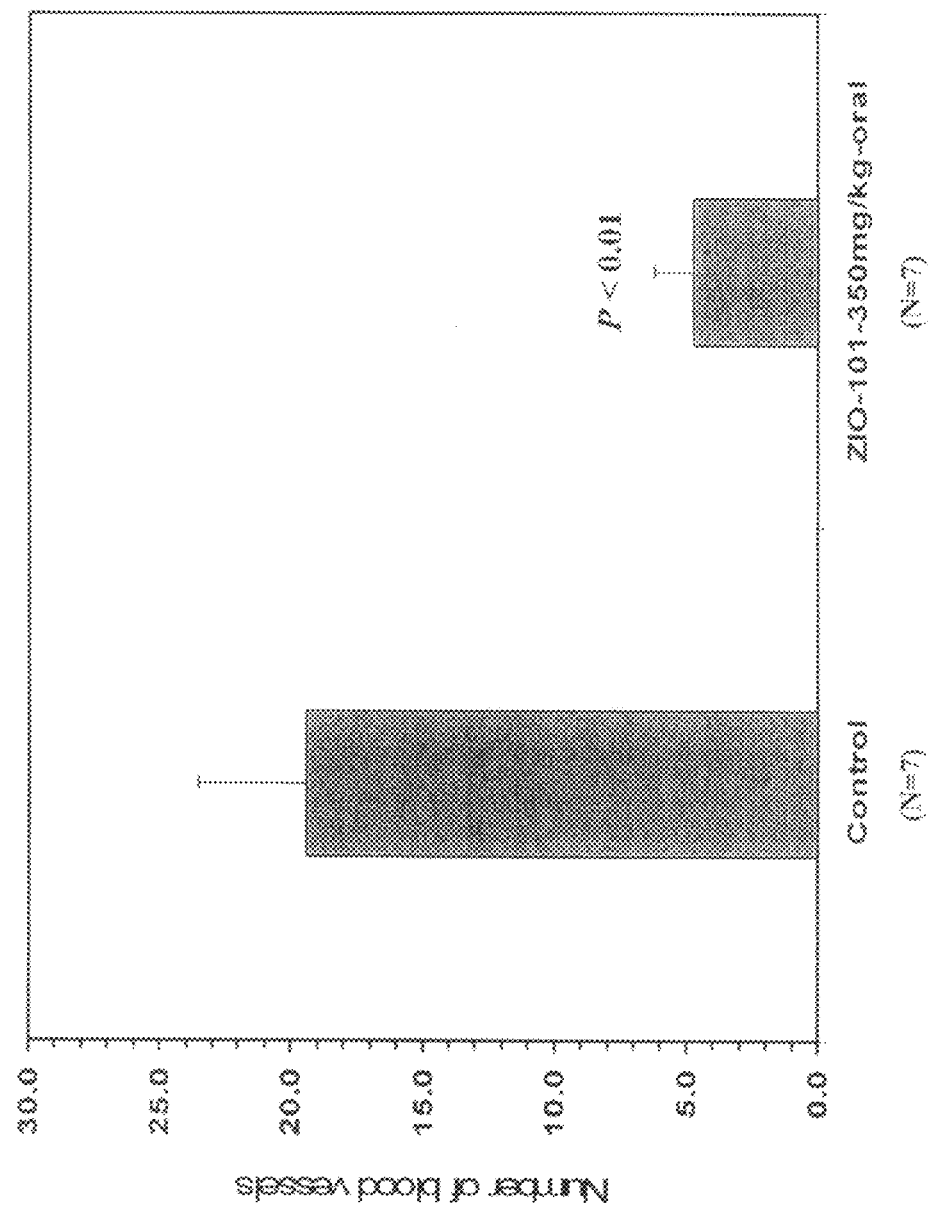
FIG. 5 shows the activity of a compound of formula (II) as measured with an in vivo Matrigel Plug assay as compared to a control measurement.
Figure 6:
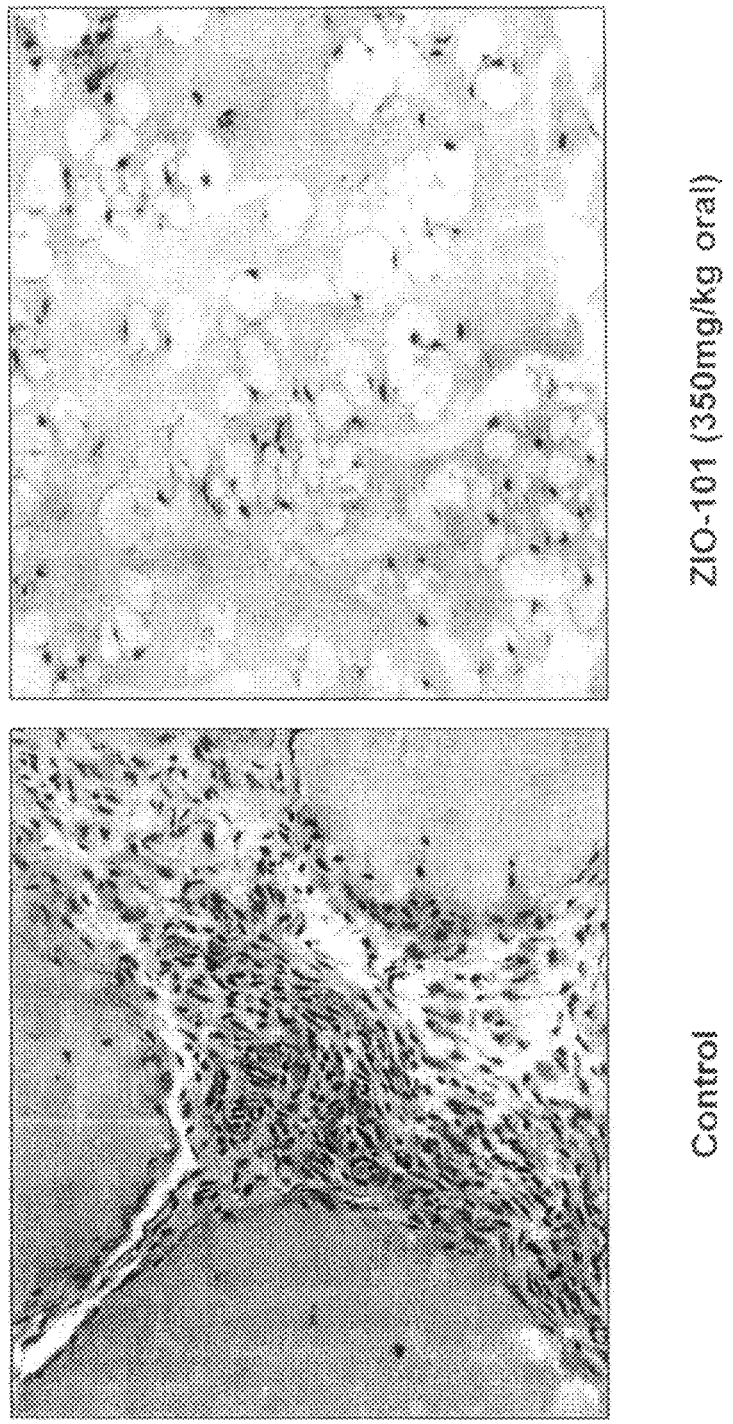
FIG. 6 shows two photographs that demonstrate a reduction in angiogenesis when a compound of formula (II) is used as measured with an in vivo Matrigel Plug assay.

Male CD2F1 mice were used for the Matrigel Plug experiment. There were two groups of mice, five mice in each group, with one group serving as a control and the second group was treated once daily for 9 days with a compound of formula II at 350 mg/kg/dose (0.2 mL/10 g of body weight) by oral administration in a saline solution. The control group received oral saline as a vehicle. Each mouse received two Matrigel plugs. On Day 0, 500 μL Matrigel at 4° C. was subcutaneously injected to each side of the mouse, wherein the injection area was shaved. The injection was done rapidly with an appropriate size needle (21 G-25 G) to ensure the entire contents of the syringe were delivered in one plug. The injected Matrigel rapidly formed a single solid gel plug. On Day 14, the mice were euthanized and the mouse skin was pulled back to expose the plug. The plugs were dissected out and fixed in 10% formalin for histological analysis. Sections of 5 μm from paraffin-embedded plugs were stained with haematoxylin and eosin (H&E) stain. Blood vessel density in a cross sectional area of each Matrigel plug was analyzed using Image Pro-Plus software. Each of the plugs was fixed in 10% formalin. Results of the assay are shown in FIGS. 5 and 6, which demonstrate that a compound of formula (II) is effective in reducing angiogenesis as compared to the control.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

The invention claimed is:

1. A method for treating endometriosis comprising administering to a patient in need thereof a compound having the structure of formula (I) or a pharmaceutically acceptable salt thereof:

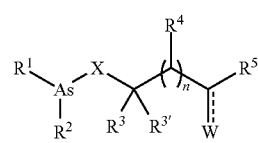

wherein
X is S or Se;
W is O, S, or (R)(R), where each occurrence of R is independently H or $C_{1-2}$alkyl;
n is 0, 1 or an integer from 2 to 20;
$R^1$ and $R^2$ are each independently $C_{1-10}$alkyl;
$R^3$ is H, $C_{1-10}$alkyl, or $C_{0-6}$alkyl-COOR$^6$;
$R^{3'}$ is H, amino, cyano, halogen, aryl, aralkyl, heteroaryl, heteroaralkyl, carboxyl, $C_{1-10}$alkyl, $C_{1-10}$alkenyl, or $C_{1-10}$alkynyl;
$R^4$ is —OH, —H, —CH$_3$, amino, —OC(O)C$_{1-10}$aralkyl, —OC(O)C$_{1-10}$alkyl, —OC(O)aryl, or a glutamine substituent; and
$R^5$ is —OH, cyano, $C_{1-6}$alkoxy, amino, O—C$_{1-10}$alkyl, O-aralkyl, —OC(O)C$_{1-10}$aralkyl, —OC(O)C$_{1-10}$alkyl, —OC(O)aryl, or a glycine substituent; and
$R^6$ is H or $C_{1-10}$alkyl; or
a compound having a structure of formula (III) or a pharmaceutically acceptable salt thereof

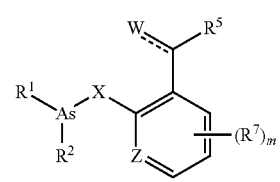

wherein
X is S or Se;
W is O, S, or (R)(R), where each occurrence of R is independently H or a $C_{1-2}$alkyl;
Z is CH or N;
$R^1$ and $R^2$ are independently $C_{1-10}$alkyl, preferably $R^1$ and $R^2$ are independently selected from methyl, ethyl, propyl, and isopropyl; and
$R^5$ is —OH, cyano, $C_{1-10}$alkoxy, amino, O-aralkyl, O-aralkyl, —OC(O)C$_{1-10}$aralkyl, —OC(O)C$_{1-10}$alkyl, —OC(O)aryl, or a glycine substituent;
$R^6$ is H or $C_{1-10}$alkyl;
$R^7$ is selected from halogen, —OH, $C_{0-6}$alkyl-COOR$^6$, $C_{1-6}$alkyl, $C_{1-6}$alkoxy, amino, amido, cyano, and nitro;
m is an integer from 0 to 4.

2. The method of claim 1, wherein W is (R)(R) and each occurrence of R is H or $C_{1-2}$alkyl.

3. The method of claim 1, wherein $R^1$ and $R^2$ are the same and are together selected from methyl, ethyl, propyl, and isopropyl.

4. The method of claim 1, wherein in a compound of formula (I) $R^3$ and $R^{3'}$ are independently H or $C_{1-10}$alkyl.

5. The method of claim 1, wherein in a compound of formula (I) $R^4$ is selected from —OH, —OC(O)C$_{1-10}$aralkyl, —OC(O)C$_{1-10}$alkyl, and —OC(O)aryl.

6. The method of claim 1, wherein X is S and in a compound of formula (I) n is 1 or an integer from 9 to 15, or in a compound of formula (III) m is 0.

7. The method of claim 1, wherein $R^5$ is selected from —OH, $C_{1-6}$alkoxy, amino, O—$C_{1-10}$alkyl, O-aralkyl, —OC(O)$C_{1-10}$aralkyl, —OC(O)$C_{1-10}$alkyl, and —OC(O)aryl.

8. The method of claim 1, wherein in a compound of formula (I) $R^6$ is $C_{1-10}$alkyl.

9. The method of claim 1, wherein in a compound of formula (I) $R^4$ is amino.

10. The method of claim 1, wherein W is O.

11. The method of claim 1, wherein the compound is selected from

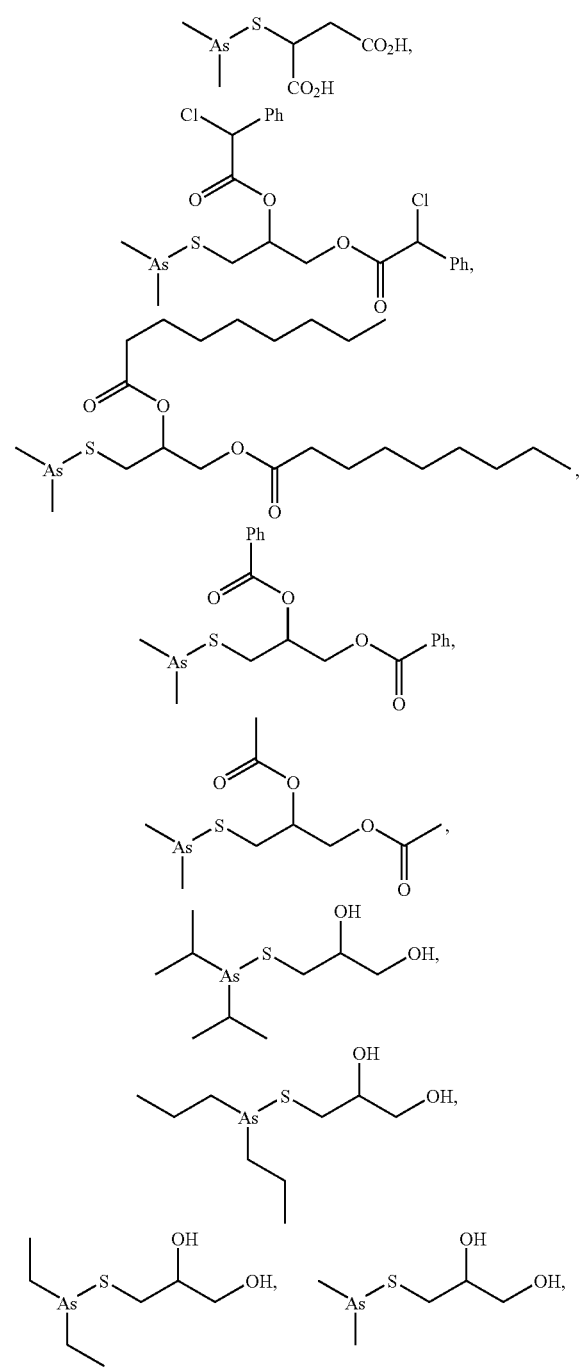

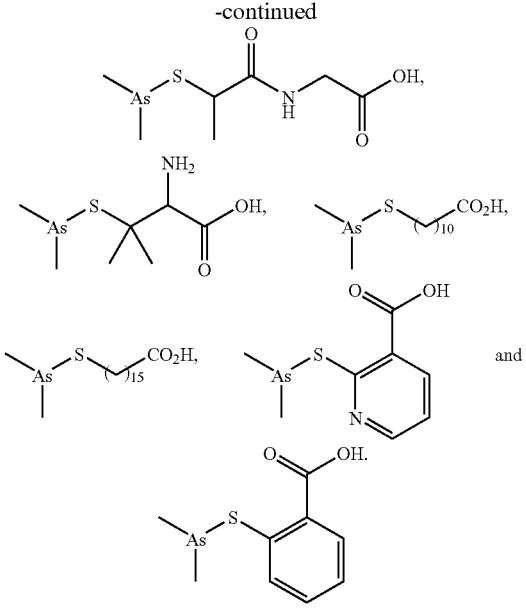

12. A method for treating endometriosis comprising administering to a patient in need thereof a compound having a structure of formula (II) or a pharmaceutically acceptable salt thereof:

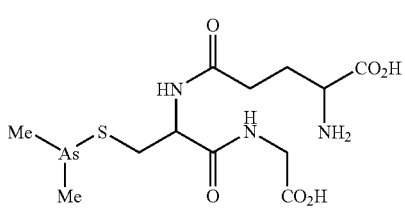

(II)

wherein the compound is administered in a crystalline form having a melting point greater than 125° C.

13. The method of claim 12, wherein the compound is administered in a crystalline form having a melting point greater than 135° C.

14. The method of claim 12, wherein the compound is administered in a crystalline form having a melting point in the range of 135-140° C.

15. The method of claim 12, wherein the compound is administered in a crystalline form having a melting point in the range of 160-220° C.

16. The method of claim 1 or 12, wherein said compound is administered one or more times daily.

17. The method of claim 1 or 12, wherein said compound is administered by injection.

18. The method of claim 1 or 12, wherein said compound is administered intravenously.

19. The method claim 1 or 12, wherein said compound is administered orally.

20. The method of claim 1, wherein in a compound of formula (I) $R^4$ is a glutamine substituent.

* * * * *